(12) United States Patent
Merritt et al.

(10) Patent No.: US 11,123,019 B2
(45) Date of Patent: Sep. 21, 2021

(54) AUTOMATED IDENTIFICATION AND CLASSIFICATION OF INTRAVASCULAR LESIONS

(71) Applicant: VOLCANO CORPORATION, San Diego, CA (US)

(72) Inventors: Fergus Merritt, Escondido, CA (US); Andrew Tochterman, Carlsbad, CA (US); Jacqueline Keller, San Diego, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 566 days.

(21) Appl. No.: 14/961,656

(22) Filed: Dec. 7, 2015

(65) Prior Publication Data
US 2016/0157787 A1  Jun. 9, 2016

Related U.S. Application Data

(60) Provisional application No. 62/089,090, filed on Dec. 8, 2014.

(51) Int. Cl.
*A61B 5/00* (2006.01)
*A61B 5/02* (2006.01)
(Continued)

(52) U.S. Cl.
CPC .......... *A61B 5/7271* (2013.01); *A61B 1/3137* (2013.01); *A61B 5/0073* (2013.01);
(Continued)

(58) Field of Classification Search
CPC .. A61B 1/3137; A61B 5/0073; A61B 5/02007
See application file for complete search history.

(56) References Cited

U.S. PATENT DOCUMENTS 5,474,074 A * 12/1995 Suorsa ............... A61B 8/12
  29/25.35
7,930,014 B2 * 4/2011 Huennekens ...... A61B 6/504
  382/159

(Continued)

FOREIGN PATENT DOCUMENTS

JP  2007075141 A  3/2007
WO 2012014212 A2  2/2012
(Continued)

*Primary Examiner* — Rajeev P Siripurapu
*Assistant Examiner* — Michael A Catina

(57) ABSTRACT

Devices, systems, and methods of mapping a vessel system of a patient and identifying lesions therein are disclosed. This includes a method of evaluating a vessel of a patient, the method comprising obtaining image data for the vessel of the patient, obtaining physiological measurements for the vessel of the patient, co-registering the obtained physiological measurements with the obtained image data such that the physiological measurements are associated with corresponding portions of the vessel of the patient, analyzing the co-registered physiology measurements to determine a classification of a lesion within the vessel of the patient, and outputting, to a user interface, the classification of the lesion. Other associated methods, systems, and devices are also provided herein.

14 Claims, 11 Drawing Sheets

(51) Int. Cl.
*A61B 5/0215* (2006.01)
*A61B 5/026* (2006.01)
*A61B 5/06* (2006.01)
*A61B 1/313* (2006.01)
*G16H 20/40* (2018.01)
*G16H 30/40* (2018.01)
*G16H 50/20* (2018.01)
*A61B 6/00* (2006.01)
*A61B 6/03* (2006.01)
*A61B 6/12* (2006.01)
*A61B 8/08* (2006.01)
*A61B 8/12* (2006.01)

(52) U.S. Cl.
CPC .......... *A61B 5/026* (2013.01); *A61B 5/02007* (2013.01); *A61B 5/0215* (2013.01); *A61B 5/02152* (2013.01); *A61B 5/066* (2013.01); *A61B 5/7425* (2013.01); *G16H 20/40* (2018.01); *G16H 30/40* (2018.01); *G16H 50/20* (2018.01); *A61B 6/032* (2013.01); *A61B 6/12* (2013.01); *A61B 6/504* (2013.01); *A61B 8/0891* (2013.01); *A61B 8/12* (2013.01)

(56) References Cited

U.S. PATENT DOCUMENTS

| | | |
|---|---|---|
| 2007/0135707 A1 | 6/2007 | Redel |
| 2007/0260141 A1* | 11/2007 | Margolis ............ A61B 5/02007 600/437 |
| 2008/0103389 A1* | 5/2008 | Begelman ................. G06T 7/62 600/425 |
| 2008/0188962 A1 | 8/2008 | Suryanarayanan |
| 2008/0221442 A1 | 9/2008 | Tolkowsky |
| 2012/0230565 A1 | 9/2012 | Steinberg |
| 2013/0046190 A1* | 2/2013 | Davies .................... A61B 5/742 600/486 |
| 2014/0039276 A1 | 2/2014 | Hattangadi |
| 2014/0187920 A1 | 7/2014 | Millett |
| 2014/0236011 A1 | 8/2014 | Fan |
| 2015/0025330 A1 | 1/2015 | Davies |
| 2015/0025398 A1 | 1/2015 | Davies |
| 2015/0032435 A1 | 1/2015 | Yagi |
| 2015/0119705 A1 | 4/2015 | Anderson |
| 2016/0007866 A1 | 1/2016 | Tochterman |
| 2016/0073972 A1 | 3/2016 | Alpert |

FOREIGN PATENT DOCUMENTS

| | | |
|---|---|---|
| WO | 2012093260 A1 | 7/2012 |
| WO | 2012093266 A1 | 7/2012 |
| WO | 2013028612 A2 | 2/2013 |
| WO | 2014175853 A1 | 10/2014 |

\* cited by examiner

AUTOMATED IDENTIFICATION AND CLASSIFICATION OF INTRAVASCULAR LESIONS

CROSS REFERENCE TO RELATED APPLICATIONS

The present application claims priority to and the benefit of the U.S. Provisional Patent Application No. 62/089,090, filed Dec. 8, 2014, which is hereby incorporated by reference in its entirety.

TECHNICAL FIELD

The present disclosure relates generally to the assessment of vessels for percutaneous coronary intervention (PCI) planning. For example, some embodiments of the present disclosure are configured to automatically label vessels of a patient in an image and identify and/or classify lesions present within the vessels to assist in diagnosing the. As a result, treatment options can tailored to the specific characteristics of the patient's lesion(s) and, thereby, improve the effectiveness of patient treatments.

BACKGROUND

Currently accepted techniques for assessing the severity of a stenosis in a blood vessel include obtaining images and physiological measurements of the vessel. For example, the severity of a stenosis is sometimes observed visually and roughly estimated based on user experience. For example, a patient's vasculature can be visualized using angiography. However, even with experience and expertise, the locations of stenoses in a vessel can be difficult to visualize in a grayscale angiographic image. The use of pressure data can improve the interpretation of information gleaned from an angiogram. For example, fractional flow reserve (FFR) and/or instantaneous wave-free ratio (iFR) can be utilized to estimate the severity of a stenosis. FFR and iFR are calculations of the ratio of a distal pressure measurement (taken on the distal side of the stenosis) relative to a proximal pressure measurement (taken on the proximal side of the stenosis). Both FFR and iFR provide an index of stenosis severity that allows determination as to whether the blockage significantly limits blood flow within the vessel to an extent that treatment is required. Further, a more complete diagnosis of the patient can be made by also performing intravascular imaging, such as intravascular ultrasound (IVUS) or optical coherence tomography (OCT). For example, in some instances intravascular imaging can be utilized to provide a cross-sectional image of the vessel and/or characterize the type(s) of tissue/plaque present in a stenosis. Due to the variations and, often, lack of clarity in angiographic and intravascular images, these diagnostic techniques require extensive training and experience before a user can confidently identify particular vessels, let alone identify and classify lesions within those vessels. However, the limited amount of time for training new medical personnel results in many patients becoming de facto training cases for the medical personnel, which can result in mis-identification of vessels, failure to identify significant lesions, and/or misclassification of identified lesions. As a result, the treatment plans selected for the patient may not be optimized for the patient's actual medical needs.

Accordingly, there remains a need for improved devices, systems, and methods for assessing the severity of a blockage in a vessel and, in particular, a stenosis in a blood vessel.

Moreover, there remains a need for improved devices, systems, and methods of automatically mapping vessel systems, identifying potential lesions in the vessel system, and classifying the identified lesions in a user friendly manner.

SUMMARY

Embodiments of the present disclosure are directed to mapping a vessel system of a patient and identifying lesions therein. One general aspect includes a method of evaluating a vessel of a patient, the method comprising: obtaining image data for the vessel of the patient; obtaining physiological measurements for the vessel of the patient; co-registering the obtained physiological measurements with the obtained image data such that the physiological measurements are associated with corresponding portions of the vessel of the patient; analyzing the co-registered physiology measurements to determine a classification of a lesion within the vessel of the patient; and outputting, to a user interface, the classification of the lesion.

In one embodiment, the above method further comprises analyzing the co-registered physiology measurements to determine a location of the lesion within the vessel of the patient. Furthermore, outputting the classification of the lesion to the user interface may include overlaying a representation of the classification onto an image of the vessel in proximity of the location of the lesion. The method may further comprise analyzing the obtained image data to identify a vessel name for the vessel and outputting, to the user interface, the vessel name in proximity to the vessel.

In an aspect, analyzing the obtained image data to identify the vessel name for the vessel includes utilizing a computer aided detection algorithm. The obtained image data may include image data received from an extravascular imaging system. Furthermore, the obtained image data may include at least one of a two-dimensional angiographic image, a three-dimensional angiographic image, or a computed tomography angiographic (CTA) image. The obtained physiological measurements may include pressure measurements, and at least some of the obtained pressure measurements may be obtained at multiple locations along the vessel. The obtained physiological measurements may also include flow measurements.

A system for evaluating a vessel of a patient is also provided, the system comprising: a processing system in communication with at least one intravascular device, the processing system configured to: obtain image data for the vessel of the patient; obtain physiological measurements for the vessel of the patient; co-register the obtained physiological measurements with the obtained image data such that the physiological measurements are associated with corresponding portions of the vessel of the patient; analyze the co-registered physiology measurements to determine a classification of a lesion within the vessel of the patient; and output, to a user interface, the classification of the lesion.

In an aspect, the processing system is further configured to analyze the co-registered physiology measurements to determine a location of the lesion within the vessel of the patient. Furthermore, the processing system may be configured to output the classification of the lesion to the user interface by overlaying a representation of the classification onto an image of the vessel in proximity of the location of the lesion. The processing system may be further configured to analyze the obtained image data to identify a vessel name for the vessel and output, to the user interface, the vessel name in proximity to the vessel.

In one embodiment, the processing system utilizes a computer aided detection algorithm to identify the vessel name for the vessel. Furthermore, the obtained image data may include image data received from an extravascular imaging system, or at least one of a two-dimensional angiographic image, a three-dimensional angiographic image, or a computed tomography angiographic (CTA) image. In an aspect, the at least one intravascular devices includes a pressure-sensing intravascular device and wherein the obtained physiological measurements include pressure measurements. The processing system may be further configured to calculate a pressure ratio based on the obtained pressure measurements. The at least one intravascular devices may also include a flow-sensing intravascular device and wherein the obtained physiological measurements include flow measurements.

BRIEF DESCRIPTION OF THE DRAWINGS

Illustrative embodiments of the present disclosure will be described with reference to the accompanying drawings, of which.

Figure 1:
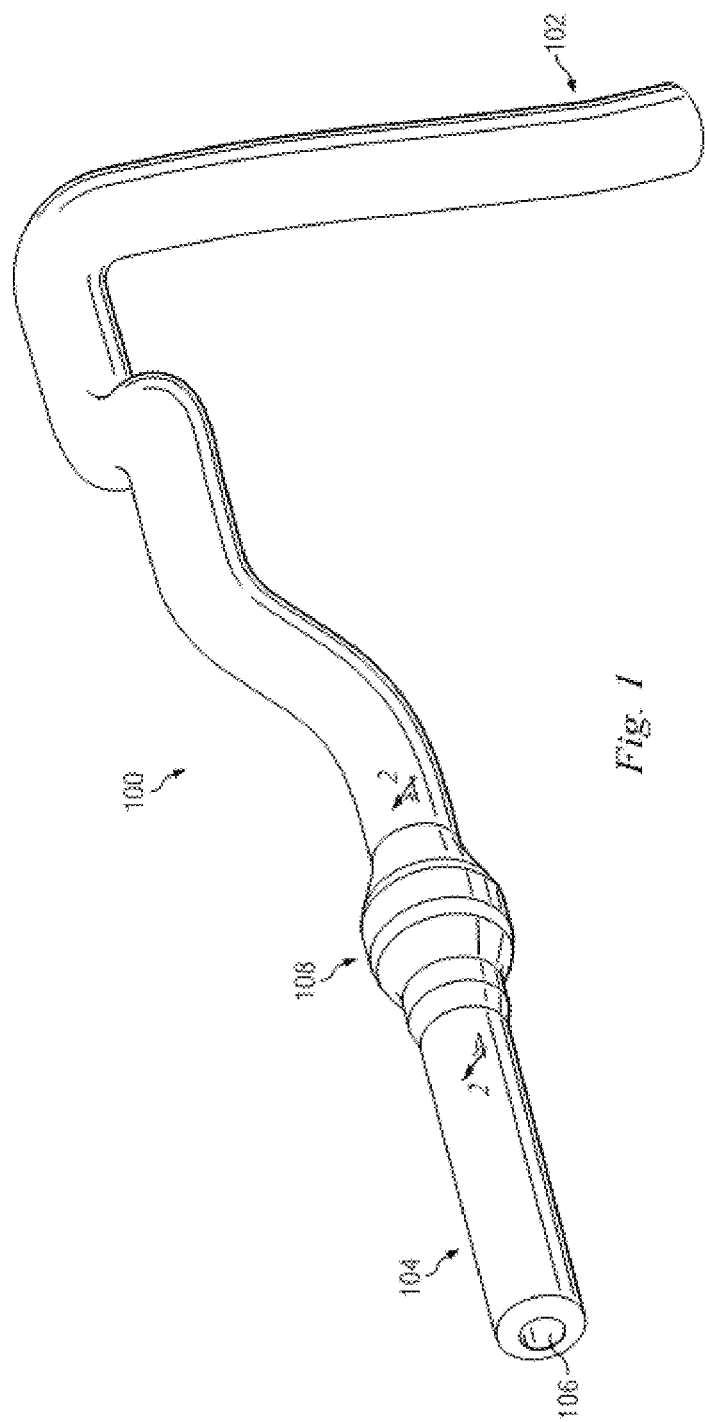
FIG. 1 is a diagrammatic perspective view of a vessel having a stenosis according to an embodiment of the present disclosure.

These drawings may be better understood by reference to the following detailed description.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Physiological measurement data and the coronary angiogram typically behave as complementary, yet segregated sources of information. The coronary angiogram has been used to make treatment decisions. More recently, physiological data (including, but not limited to, pressure and/or flow measurements, both at hyperemia and rest) have shown that better decisions can be made based on the severity of a blockage by measuring the change in underlying physiological conditions from the beginning of a target artery to the end. Treating a patient based on the severity of this change or delta has shown to improve outcomes and reduce waste from unnecessary procedures. In one or more aspects of the present disclosure, the physiological data, as collected real-time, is linked or co-registered to a schematic of the coronary arteries or an angiogram. At this point, a computer aided detection algorithm can be applied to the data to identify and map coronary vessels. Physiological measurements obtained from within the vessels can then be compared to the map to identify lesion locations. Further, the physiological measurements can be utilized to determine a length and/or classify the identified lesions. In making the classification, data representing the lesion sites may also be visually depicted in a way that allows a clinician to interact and assess the severity and/or boundaries of the lesion. Furthermore, the identification and classification of the lesions in the vessel system can be displayed to a clinician on a user interface. Among other benefits, the identification and classification of the lesions can permit a clinician to plan a percutaneous coronary intervention tailored to the specific lesion characteristics of the patient.

Figure 2:
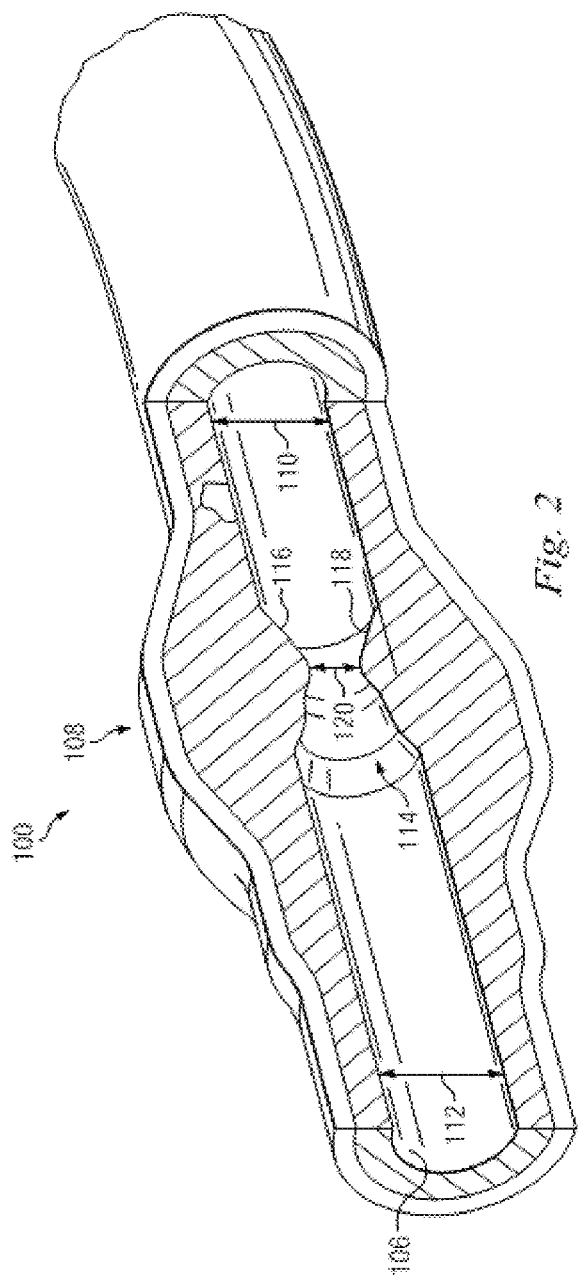
FIG. 2 is a diagrammatic, partial cross-sectional perspective view of a portion of the vessel of FIG. 1 taken along section line 2-2 of FIG. 1.

Referring to FIGS. 1 and 2, shown therein is a vessel 100 having a stenosis according to an embodiment of the present disclosure. In that regard, FIG. 1 is a diagrammatic perspective view of the vessel 100, while FIG. 2 is a partial cross-sectional perspective view of a portion of the vessel 100 taken along section line 2-2 of FIG. 1. Referring more specifically to FIG. 1, the vessel 100 includes a proximal portion 102 and a distal portion 104. A lumen 106 extends along the length of the vessel 100 between the proximal portion 102 and the distal portion 104. In that regard, the lumen 106 is configured to allow the flow of fluid through the vessel. In some instances, the vessel 100 is a blood vessel. In some particular instances, the vessel 100 is a coronary artery. In such instances, the lumen 106 is configured to facilitate the flow of blood through the vessel 100.

As shown, the vessel 100 includes a stenosis 108 between the proximal portion 102 and the distal portion 104. Stenosis 108 is generally representative of any blockage or other structural arrangement that results in a restriction to the flow of fluid through the lumen 106 of the vessel 100. Embodiments of the present disclosure are suitable for use in a wide variety of vascular applications, including without limitation coronary, peripheral (including but not limited to lower limb, carotid, and neurovascular), renal, and/or venous. Where the vessel 100 is a blood vessel, the stenosis 108 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow.

Referring more particularly to FIG. 2, the lumen 106 of the vessel 100 has a diameter 110 proximal of the stenosis 108 and a diameter 112 distal of the stenosis. In some instances, the diameters 110 and 112 are substantially equal to one another. In that regard, the diameters 110 and 112 are intended to represent healthy portions, or at least healthier portions, of the lumen 106 in comparison to stenosis 108. Accordingly, these healthier portions of the lumen 106 are illustrated as having a substantially constant cylindrical profile and, as a result, the height or width of the lumen has been referred to as a diameter. However, it is understood that in many instances these portions of the lumen 106 will also have plaque buildup, a non-symmetric profile, and/or other irregularities, but to a lesser extent than stenosis 108 and, therefore, will not have a cylindrical profile. In such instances, the diameters 110 and 112 are understood to be representative of a relative size or cross-sectional area of the lumen and do not imply a circular cross-sectional profile.

As shown in FIG. 2, stenosis 108 includes plaque buildup 114 that narrows the lumen 106 of the vessel 100. In some instances, the plaque buildup 114 does not have a uniform or symmetrical profile, making angiographic evaluation of such a stenosis unreliable. In the illustrated embodiment, the plaque buildup 114 includes an upper portion 116 and an opposing lower portion 118. In that regard, the lower portion 118 has an increased thickness relative to the upper portion 116 that results in a non-symmetrical and non-uniform profile relative to the portions of the lumen proximal and distal of the stenosis 108. As shown, the plaque buildup 114 decreases the available space for fluid to flow through the lumen 106. In particular, the cross-sectional area of the lumen 106 is decreased by the plaque buildup 114. At the narrowest point between the upper and lower portions 116, 118 the lumen 106 has a height 120, which is representative of a reduced size or cross-sectional area relative to the diameters 110 and 112 proximal and distal of the stenosis 108. Note that the stenosis 108, including plaque buildup 114 is exemplary in nature and should be considered limiting in any way. In that regard, it is understood that the stenosis 108 has other shapes and/or compositions that limit the flow of fluid through the lumen 106 in other instances. While the vessel 100 is illustrated in FIGS. 1 and 2 as having a single stenosis 108 and the description of the embodiments below is primarily made in the context of a single stenosis, it is nevertheless understood that the devices, systems, and methods described herein have similar application for a vessel having multiple stenosis regions.

Figure 3:
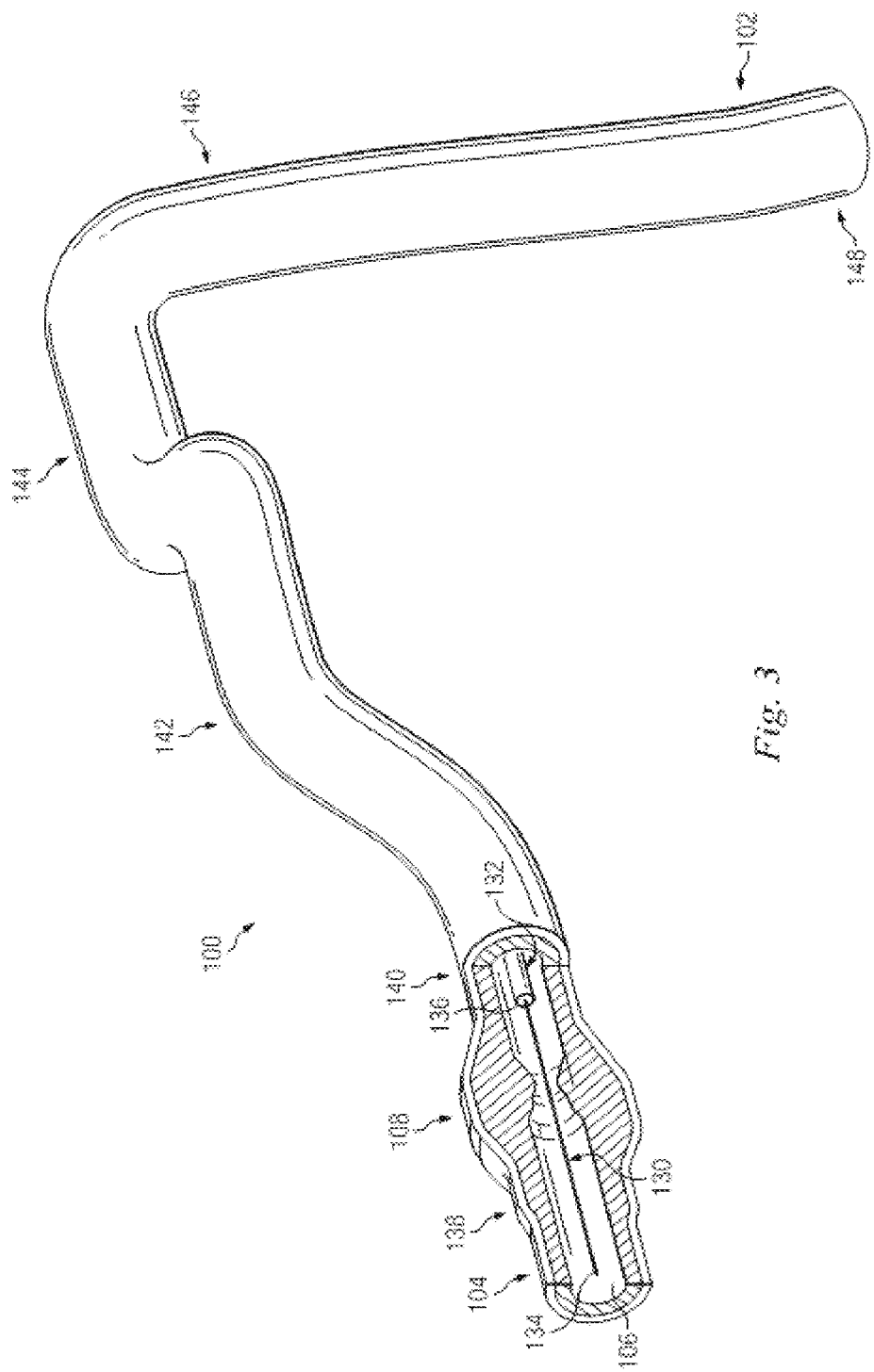
FIG. 3 is a diagrammatic, partial cross-sectional perspective view of the vessel of FIGS. 1 and 2 with instruments positioned therein according to an embodiment of the present disclosure.

Referring now to FIG. 3, the vessel 100 is shown with instruments 130 and 132 positioned therein according to an embodiment of the present disclosure. In general, instruments 130 and 132 may be any form of device, instrument, or probe sized and shaped to be positioned within a vessel. In the illustrated embodiment, instrument 130 is generally representative of a guide wire, while instrument 132 is generally representative of a catheter. In that regard, instrument 130 extends through a central lumen of instrument 132. However, in other embodiments, the instruments 130 and 132 take other forms. In that regard, the instruments 130 and 132 are of similar form in some embodiments. For example, in some instances, both instruments 130 and 132 are guide wires. In other instances, both instruments 130 and 132 are catheters. On the other hand, the instruments 130 and 132 are of different form in some embodiments, such as the illustrated embodiment, where one of the instruments is a catheter and the other is a guide wire. Further, in some instances, the instruments 130 and 132 are disposed coaxial with one another, as shown in the illustrated embodiment of FIG. 3. In other instances, one of the instruments extends through an off-center lumen of the other instrument. In yet other instances, the instruments 130 and 132 extend side-by-side. In some particular embodiments, at least one of the instruments is as a rapid-exchange device, such as a rapid-exchange catheter. In such embodiments, the other instrument is a buddy wire or other device configured to facilitate the introduction and removal of the rapid-exchange device. Further still, in other instances, instead of two separate instruments 130 and 132 a single instrument is utilized. In some embodiments, the single instrument incorporates aspects of the functionalities (e.g., data acquisition) of both instruments 130 and 132.

Instrument 130 is configured to obtain diagnostic information about the vessel 100. In that regard, the instrument 130 includes one or more sensors, transducers, and/or other monitoring elements configured to obtain the diagnostic information about the vessel. The diagnostic information includes one or more of pressure, flow (velocity and/or volume), images (including images obtained using ultrasound (e.g., IVUS), OCT, thermal, and/or other imaging techniques), temperature, and/or combinations thereof. The one or more sensors, transducers, and/or other monitoring elements are positioned adjacent a distal portion of the instrument 130 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 134 of the instrument 130 in some instances. In some instances, at least one of the one or more sensors, transducers, and/or other monitoring elements is positioned at the distal tip of the instrument 130.

The instrument 130 can include at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Examples of commercially available guide wire products that include suitable pressure monitoring elements include, without limitation, the Verrata® pressure guide wire, the PrimeWire Prestige® PLUS pressure guide wire, and the ComboWire® XT pressure and flow guide wire, each available from Volcano Corporation, as well as the PressureWire™ Certus guide wire and the PressureWire™ Aeris guide wire, each available from St. Jude Medical, Inc. Generally, the instrument 130 is sized such that it can be positioned through the stenosis 108 without significantly impacting fluid flow across the stenosis, which would impact the distal pressure reading. Accordingly, in some instances the instrument 130 has an outer diameter of 0.018" or less. In some embodiments, the instrument 130 has an outer diameter of 0.014" or less. In some embodiments, the instrument 130 has an outer diameter of 0.035" or less.

Instrument 132 is also configured to obtain diagnostic information about the vessel 100. In some instances, instrument 132 is configured to obtain the same diagnostic information as instrument 130. In other instances, instrument 132 is configured to obtain different diagnostic information than instrument 130, which may include additional diagnostic information, less diagnostic information, and/or alternative diagnostic information. The diagnostic information obtained by instrument 132 includes one or more of pressure, flow (velocity and/or volume), images (including images obtained using ultrasound (e.g., IVUS), OCT, thermal, and/or other imaging techniques), temperature, and/or combinations thereof. Instrument 132 includes one or more sensors, transducers, and/or other monitoring elements configured to obtain this diagnostic information. In that regard, the one or more sensors, transducers, and/or other monitoring elements are positioned adjacent a distal portion of the instrument 132 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 136 of the instrument 132 in some instances. In some instances, at least one of the one or more sensors, transducers, and/or other monitoring elements is positioned at the distal tip of the instrument 132.

Similar to instrument 130, instrument 132 can also include at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Currently available catheter products suitable for use with one or more of Siemens AXIOM Sensis, Mennen Horizon XVu, and Philips Xper IM Physiomonitoring 5 and include pressure monitoring elements can be utilized for instrument 132 in some instances.

In accordance with aspects of the present disclosure, at least one of the instruments 130 and 132 is configured to monitor a pressure within the vessel 100 distal of the stenosis 108 and at least one of the instruments 130 and 132 is configured to monitor a pressure within the vessel proximal of the stenosis. In that regard, the instruments 130, 132 are sized and shaped to allow positioning of the at least one element configured to monitor pressure within the vessel 100 to be positioned proximal and/or distal of the stenosis 108 as necessary based on the configuration of the devices. In that regard, FIG. 3 illustrates a position 138 suitable for measuring pressure distal of the stenosis 108. In that regard, the position 138 is less than 5 cm, less than 3 cm, less than 2 cm, less than 1 cm, less than 5 mm, and/or less than 2.5 mm from the distal end of the stenosis 108 (as shown in FIG. 2) in some instances. FIG. 3 also illustrates a plurality of suitable positions for measuring pressure proximal of the stenosis 108. In that regard, positions 140, 142, 144, 146, and 148 each represent a position that is suitable for monitoring the pressure proximal of the stenosis in some instances. In that regard, the positions 140, 142, 144, 146, and 148 are positioned at varying distances from the proximal end of the stenosis 108 ranging from more than 20 cm down to about 5 mm or less. Generally, the proximal pressure measurement will be spaced from the proximal end of the stenosis. Accordingly, in some instances, the proximal pressure measurement is taken at a distance equal to or greater than an inner diameter of the lumen of the vessel from the proximal end of the stenosis. In the context of coronary artery pressure measurements, the proximal pressure measurement is generally taken at a position proximal of the stenosis and distal of the aorta, within a proximal portion of the vessel. However, in some particular instances of coronary artery pressure measurements, the proximal pressure measurement is taken from a location inside the aorta. In other instances, the proximal pressure measurement is taken at the root or ostium of the coronary artery.

In some embodiments, at least one of the instruments 130 and 132 is configured to monitor pressure within the vessel 100 while being moved through the lumen 106. In some instances, instrument 130 is configured to be moved through the lumen 106 and across the stenosis 108. In that regard, the instrument 130 is positioned distal of the stenosis 108 and moved proximally (i.e., pulled back) across the stenosis to a position proximal of the stenosis in some instances. In other instances, the instrument 130 is positioned proximal of the stenosis 108 and moved distally across the stenosis to a position distal of the stenosis. Movement of the instrument 130, either proximally or distally, is controlled manually by medical personnel (e.g., hand of a surgeon) in some embodiments. In other embodiments, movement of the instrument 130, either proximally or distally, is controlled automatically by a movement control device (e.g., a pullback device, such as the Trak Back® II Device available from Volcano Corporation). In that regard, the movement control device controls the movement of the instrument 130 at a selectable and known speed (e.g., 2.0 mm/s, 1.0 mm/s, 0.5 mm/s, 0.2 mm/s, etc.) in some instances. Movement of the instrument 130 through the vessel is continuous for each pullback or push through, in some instances. In other instances, the instrument 130 is moved step-wise through the vessel (i.e., repeatedly moved a fixed amount of distance and/or a fixed amount of time). Some aspects of the visual depictions discussed below are particularly suited for embodiments where at least one of the instruments 130 and 132 is moved through the lumen 106. Further, in some particular instances, aspects of the visual depictions discussed below are particularly suited for embodiments where a single instrument is moved through the lumen 106, with or without the presence of a second instrument.

The instruments 130 and/or 132 can be used to conduct medical sensing procedures associated with Instant Wave-Free Ratio™ Functionality (iFR® Functionality) (both trademarks of Volcano Corp.) and those disclosed in U.S. patent application Ser. No. 13/460,296, entitled "DEVICES, SYSTEMS, AND METHODS FOR ASSESSING A VESSEL," hereby incorporated by reference in its entirety, which discloses the use of pressure ratios that are available without application of a hyperemic agent. Further, medical sensing procedures associated with compensated Pd/Pa ratios suitable for estimating iFR®, FFR, and/or other accepted diagnostic pressure ratios as disclosed in U.S. Provisional Patent Application No. 62/024,005, filed Jul. 14, 2014 and entitled "DEVICES, SYSTEMS, AND METHODS FOR TREATMENT OF VESSELS," which is hereby incorporated by reference in its entirety, can be conducted using the instruments 130 and/or 132.

Figure 4:
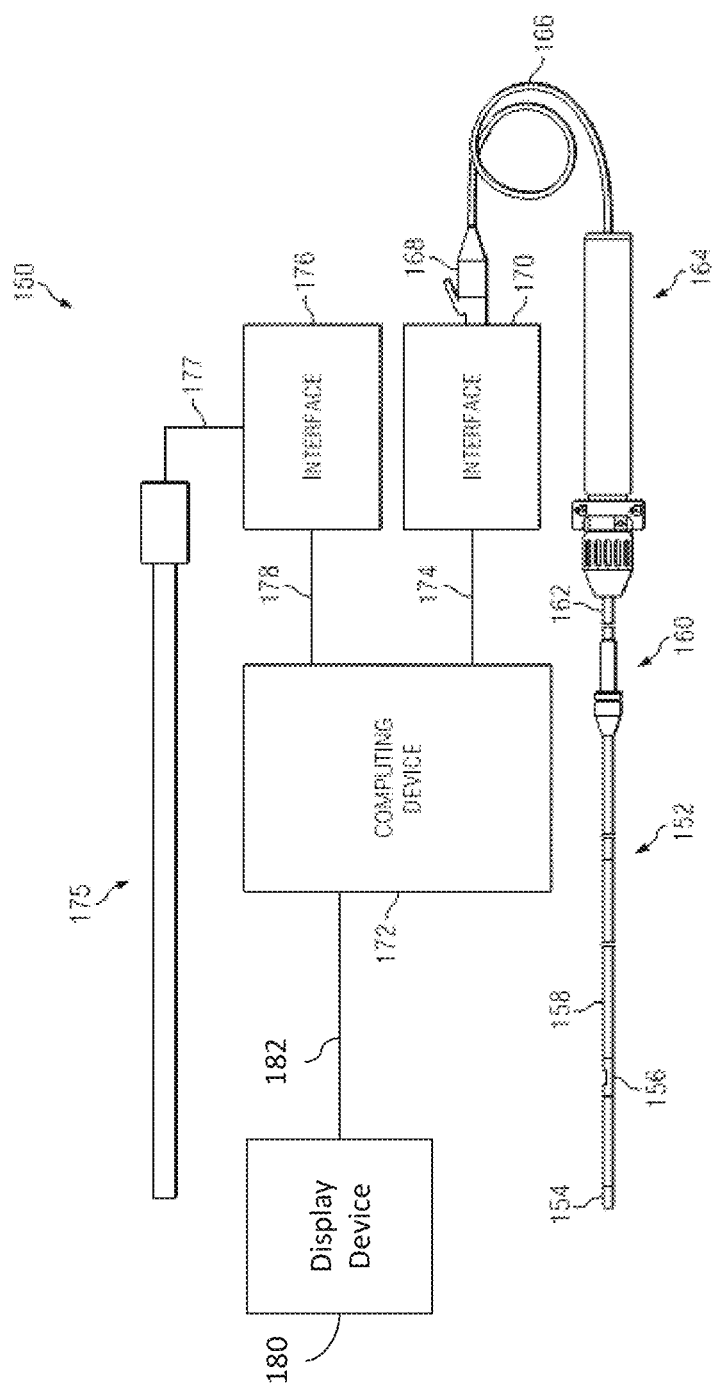
FIG. 4 is a diagrammatic, schematic view of a system according to an embodiment of the present disclosure.

Referring now to FIG. 4, shown therein is a system 150 according to an embodiment of the present disclosure. In that regard, FIG. 4 is a diagrammatic, schematic view of the system 150. As shown, the system 150 includes an instrument 152. In that regard, in some instances instrument 152 is suitable for use as at least one of instruments 130 and 132 discussed above. Accordingly, in some instances the instrument 152 includes features similar to those discussed above with respect to instruments 130 and 132 in some instances. In the illustrated embodiment, the instrument 152 is a guide wire having a distal portion 154 and a housing 156 positioned adjacent the distal portion. In that regard, the housing 156 is spaced approximately 3 cm from a distal tip of the instrument 152. The housing 156 is configured to house one or more sensors, transducers, and/or other monitoring elements configured to obtain the diagnostic information about the vessel. In the illustrated embodiment, the housing 156 contains at least a pressure sensor configured to monitor a pressure within a lumen in which the instrument 152 is positioned. A shaft 158 extends proximally from the housing 156. A torque device 160 is positioned over and coupled to a proximal portion of the shaft 158. A proximal end portion 162 of the instrument 152 is coupled to a connector 164. A cable 166 extends from connector 164 to a connector 168. In some instances, connector 168 is configured to be plugged into an interface 170. In that regard, interface 170 is a patient interface module (PIM) in some instances. In some instances, the cable 166 is replaced with a wireless connection. In that regard, it is understood that various communication pathways between the instrument 152 and the interface 170 may be utilized, including physical connections (including electrical, optical, and/or fluid connections), wireless connections, and/or combinations thereof.

The interface 170 is communicatively coupled to a computing device 172 via a connection 174. Computing device 172 is generally representative of any device suitable for performing the processing and analysis techniques discussed within the present disclosure. In some embodiments, the computing device 172 includes a processor, random access memory, and a storage medium. In that regard, in some particular instances the computing device 172 is programmed to execute steps associated with the data acquisition and analysis described herein. Accordingly, it is understood that any steps related to data acquisition, data processing, instrument control, and/or other processing or control aspects of the present disclosure may be implemented by the computing device using corresponding instructions stored on or in a non-transitory computer readable medium accessible by the computing device. In some instances, the computing device 172 is a console device. In some particular instances, the computing device 172 is similar to the s5 Imaging System or the s5i Imaging System, each available from Volcano Corporation. In some instances, the computing device 172 is portable (e.g., handheld, on a rolling cart, etc.). In some instances, all or a portion of the computing device 172 can be implemented as a bedside controller such that one or more processing steps described herein can be performed by processing component(s) of the bedside controller. An exemplary bedside controller is described in U.S. Provisional Application No. 62/049,265, titled "Bedside Controller for Assessment of Vessels and Associated Devices, Systems, and Methods," and filed Sep. 11, 2014, the entirety of which is hereby incorporated by reference herein. Further, it is understood that in some instances the computing device 172 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

Together, connector 164, cable 166, connector 168, interface 170, and connection 174 facilitate communication between the one or more sensors, transducers, and/or other monitoring elements of the instrument 152 and the computing device 172. However, this communication pathway is exemplary in nature and should not be considered limiting in any way. In that regard, it is understood that any communication pathway between the instrument 152 and the computing device 172 may be utilized, including physical connections (including electrical, optical, and/or fluid connections), wireless connections, and/or combinations thereof. In that regard, it is understood that the connection 174 is wireless in some instances. In some instances, the connection 174 includes a communication link over a network (e.g., intranet, internet, telecommunications network, and/or other network). In that regard, it is understood that the computing device 172 is positioned remote from an operating area where the instrument 152 is being used in some instances. Having the connection 174 include a connection over a network can facilitate communication between the instrument 152 and the remote computing device 172 regardless of whether the computing device is in an adjacent room, an adjacent building, or in a different state/country. Further, it is understood that the communication pathway between the instrument 152 and the computing device 172 is a secure connection in some instances. Further still, it is understood that, in some instances, the data communicated over one or more portions of the communication pathway between the instrument 152 and the computing device 172 is encrypted.

The system 150 also includes an instrument 175. In that regard, in some instances instrument 175 is suitable for use as at least one of instruments 130 and 132 discussed above. Accordingly, in some instances the instrument 175 includes features similar to those discussed above with respect to instruments 130 and 132 in some instances. In the illustrated embodiment, the instrument 175 is a catheter-type device. In that regard, the instrument 175 includes one or more sensors, transducers, and/or other monitoring elements adjacent a distal portion of the instrument configured to obtain the diagnostic information about the vessel. In the illustrated embodiment, the instrument 175 includes a pressure sensor configured to monitor a pressure within a lumen in which the instrument 175 is positioned. The instrument 175 is in communication with an interface 176 via connection 177. In some instances, interface 176 is a hemodynamic monitoring system or other control device, such as Siemens AXIOM Sensis, Mennen Horizon XVu, and Philips Xper IM Physiomonitoring 5. In one particular embodiment, instrument 175 is a pressure-sensing catheter that includes fluid column extending along its length. In such an embodiment, interface 176 includes a hemostasis valve fluidly coupled to the fluid column of the catheter, a manifold fluidly coupled to the hemostasis valve, and tubing extending between the components as necessary to fluidly couple the components. In that regard, the fluid column of the catheter is in fluid communication with a pressure sensor via the valve, manifold, and tubing. In some instances, the pressure sensor is part of interface 176. In other instances, the pressure sensor is a separate component positioned between the instrument 175 and the interface 176. The interface 176 is communicatively coupled to the computing device 172 via a connection 178.

Figure 5:
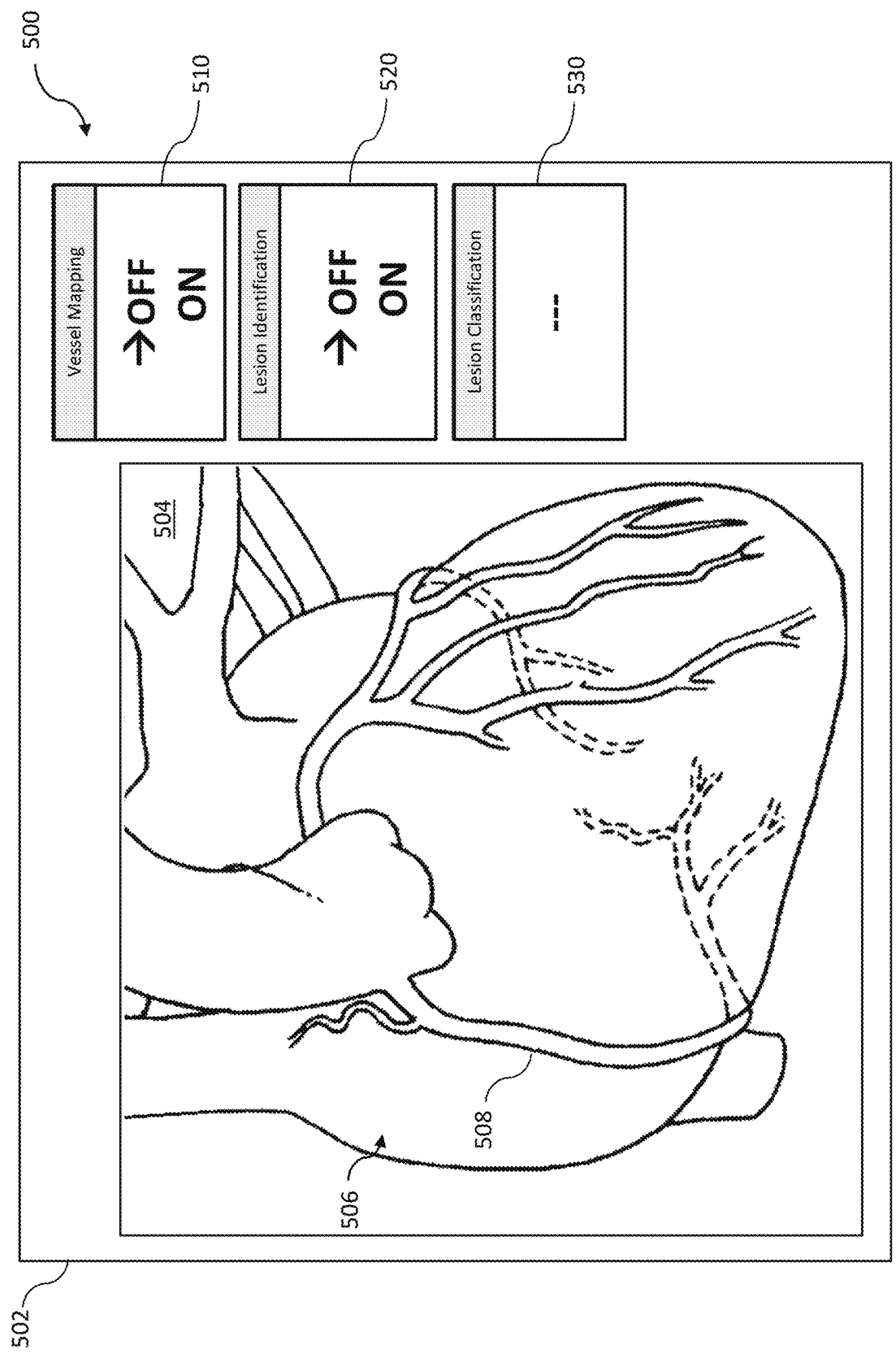
FIG. 5 is a stylized image of a patient's vasculature as seen in an angiogram image on a user interface according to an embodiment of the present disclosure.
Figure 7:
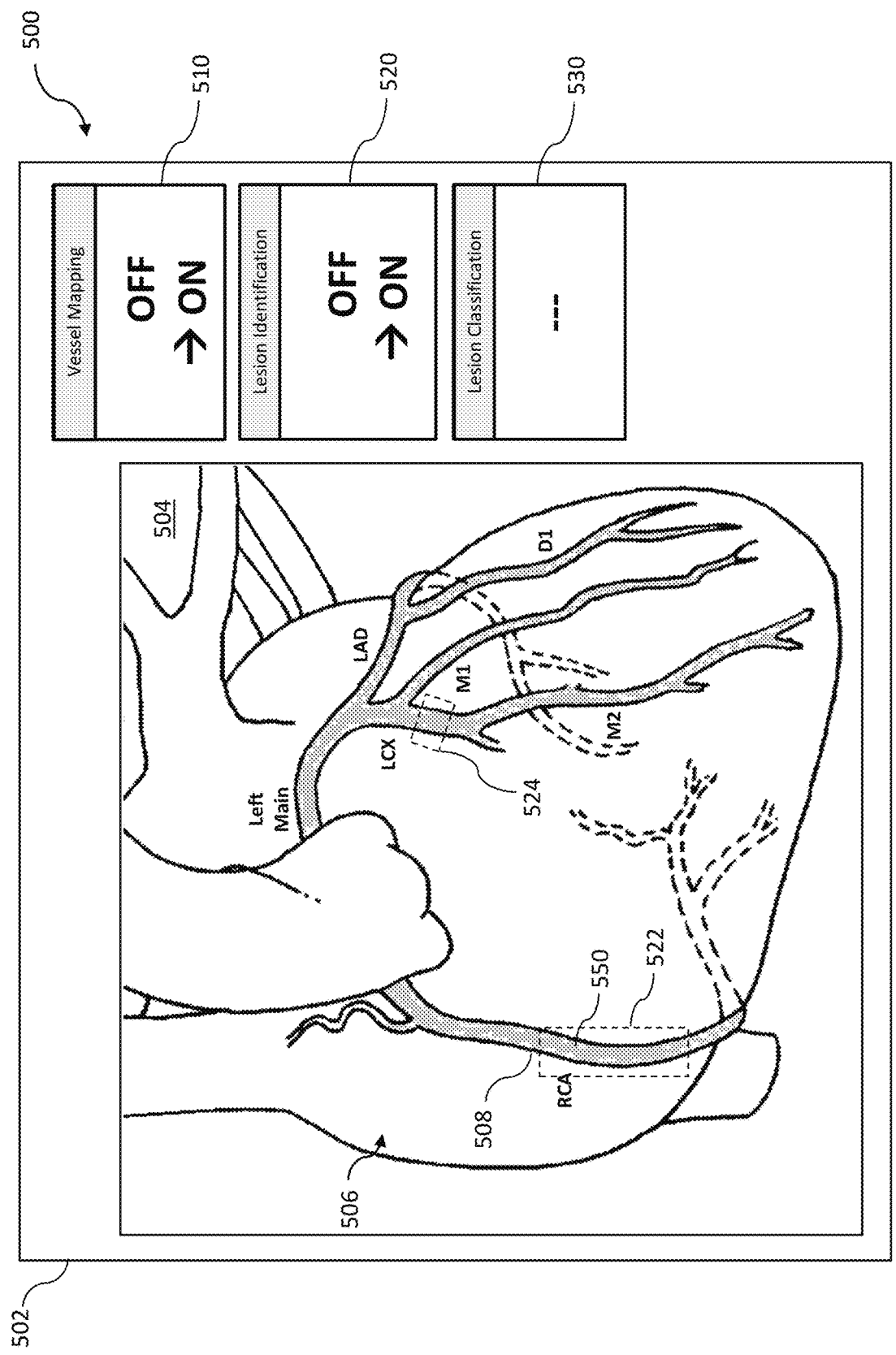
FIG. 7 is an annotated version of a patient's vasculature as seen in an angiogram image on a user interface according to another embodiment of the present disclosure.

The computing device 172 is communicatively coupled to a display device 180 via a connection 182. In some embodiments, the display device 172 is a component of the computing device 172, while in other embodiments, the display device 172 is distinct from the computing device 172. In some embodiments, the display device 172 is implemented as a bedside controller having a touch-screen display as described, for example, in U.S. Provisional Application No. 62/049,265, titled "Bedside Controller for Assessment of Vessels and Associated Devices, Systems, and Methods," and filed Sep. 11, 2014, the entirety of which is hereby incorporated by reference herein. The computing device 172 can generate screen displays including data collected by the instruments 152 and 175 and other instruments, quantities computed based on the collected data, visualizations of the vessel in which the data is collected, and visualizations based on the collected data and computed quantities. Exemplary screen displays are illustrated in FIGS. 5 and 7. The computing device 172 can provide the display data associated with the screen displays to the display device 180.

The computing device 172 can additionally be communicatively coupled to a user interface device. The user interface device permits a user to interact with the screen displays on the display device 180. For example, the user can provide a user input to modify all or a portion of the screen display using the user interface device. Exemplary user inputs and the corresponding modifications to the screen display are illustrated in FIGS. 5 and 7. In some embodiments, the user interface device is a separate component from the display device 180. In other embodiments, the user interface device is part of the display device 180. For example, the user interface device can be implemented as a bedside controller having a touch-screen display as described, for example, in U.S. Provisional Application No. 62/049,265, titled "Bedside Controller for Assessment of Vessels and Associated Devices, Systems, and Methods," and filed Sep. 11, 2014, the entirety of which is hereby incorporated by reference herein. In such embodiments, a user input can be a touch input received on the touch sensitive display of the bedside controller.

Similar to the connections between instrument 152 and the computing device 172, interface 176 and connections 177 and 178 facilitate communication between the one or more sensors, transducers, and/or other monitoring elements of the instrument 175 and the computing device 172. However, this communication pathway is exemplary in nature and should not be considered limiting in any way. In that regard, it is understood that any communication pathway between the instrument 175 and the computing device 172 may be utilized, including physical connections (including electrical, optical, and/or fluid connections), wireless connections, and/or combinations thereof. In that regard, it is understood that the connection 178 is wireless in some instances. In some instances, the connection 178 includes a communication link over a network (e.g., intranet, internet, telecommunications network, and/or other network). In that regard, it is understood that the computing device 172 is positioned remote from an operating area where the instrument 175 is being used in some instances. Having the connection 178 include a connection over a network can facilitate communication between the instrument 175 and the remote computing device 172 regardless of whether the computing device is in an adjacent room, an adjacent building, or in a different state/country. Further, it is understood that the communication pathway between the instrument 175 and the computing device 172 is a secure connection in some instances. Further still, it is understood that, in some instances, the data communicated over one or more portions of the communication pathway between the instrument 175 and the computing device 172 is encrypted.

It is understood that one or more components of the system 150 are not included, are implemented in a different arrangement/order, and/or are replaced with an alternative device/mechanism in other embodiments of the present disclosure. For example, in some instances, the system 150 does not include interface 170 and/or interface 176. In such instances, the connector 168 (or other similar connector in communication with instrument 152 or instrument 175) may plug into a port associated with computing device 172. Alternatively, the instruments 152, 175 may communicate wirelessly with the computing device 172. Generally speaking, the communication pathway between either or both of the instruments 152, 175 and the computing device 172 may have no intermediate nodes (i.e., a direct connection), one intermediate node between the instrument and the computing device, or a plurality of intermediate nodes between the instrument and the computing device.

In some embodiments, the system 150 can additionally include a bedside controller, such as the bedside controller described in U.S. Provisional Application No. 62/049,265, titled "Bedside Controller for Assessment of Vessels and Associated Devices, Systems, and Methods," and filed Sep. 11, 2014, the entirety of which is hereby incorporated by reference herein. The bedside controller may be utilized by a clinician to control instruments 152 and 175 to acquire pressure data during a procedure, watch real-time medical pressure measurements (e.g., visual representations of pressure data, such as pressure waveforms, numerical values, etc.), compute pressure ratio(s) based on the collected pressure data, and interact with the obtained medical sensing data, a visual representation of the obtained medical sensing data and/or computed pressure ratio(s), a visualization based on the obtained medical sensing data and/or computed pressure ratio(s), and/or a visual representation of the vessel 100. In that regard, the bedside controller can be communicatively coupled to the computing device 172, the interfaces 170 and 176, and/or the instruments 152 and 175.

In some embodiments, the system 150 can include an inventory database 190 associated with a clinical environment, such as a hospital or other healthcare facility at which a PCI would be carried out on a patient. The inventory database can store various data about stents that are available to a clinician for use. The data can include manufacturer names, length, diameter, material, quantity available at the hospital, quantity available for immediate use, resupply frequency, next shipment date, and other suitable information. The computing device 172 can compile a plurality of stent options based on the inventory database 190 and provide a selection menu to the clinician. The computing device 172 can provide automatically recommend a particular stent (e.g., a stent from a particular manufacturer, with a particular length, diameter, and/or material) based on the PCI planning conducted using the graphical user interface. The computing device 172 can also receive a user input selecting a particular stent and provide it into the graphical user interface such that a clinician can assess the efficacy of treatment using the selected stent. The computing device 172 is communicatively coupled to the inventory database 190 via a connection 192. The connection 192 can be representative of one or more network connections that communicatively couple the computing device 172 with a computing system of the healthcare facility.

The diagnostic information and/or data obtained by instruments 130, 132, 152, and/or 175 are correlated or co-registered to angiographic image(s) and/or other two-dimensional or three-dimensional depictions of a patient's vasculature obtained by an external imaging system. In various embodiments, the diagnostic information obtained by the external imaging system can include externally-obtained angiographic images, x-ray images, CT images, PET images, MRI images, SPECT images, and/or other two-dimensional or three-dimensional extraluminal depictions of a patient's vasculature. Spatial co-registration can be completed using techniques disclosed in U.S. Pat. No. 7,930,014, titled "VASCULAR IMAGE CO-REGISTRATION," which is hereby incorporated by reference in its entirety, based on the known pullback speed/distance, based on a known starting point, based on a known ending point, and/or combinations thereof. For example, a mechanical pullback device can be used to conduct the pressure-sensing procedure. The mechanical pullback device can move the pressure-sensing device through the vessel at a fixed, known rate. The location of the pressure measurements and/or the pressure ratio(s) can be determined based on the rate of the pullback and a known location of the pressure-sensing device (e.g., a start position, a mid-point position, an end position, available from angiography data). In some embodiments, diagnostic information and/or data is correlated to vessel images using techniques similar to those described in U.S. Provisional Patent Application No. 61/747,480, titled "SPATIAL CORRELATION OF INTRAVASCULAR IMAGES AND PHYSIOLOGICAL FEATURES" and filed Dec. 31, 2012, which is hereby incorporated by reference in its entirety. In some embodiments, co-registration and/or correlation can be completed as described in U.S. Provisional Patent Application No. 61/856,509, titled "DEVICES, SYSTEMS, AND METHODS FOR ASSESSMENT OF VESSELS" and filed Jul. 19, 2013, which is hereby incorporated by reference in its entirety.

In some embodiments, diagnostic information and/or data is correlated to vessel images using techniques similar to those described in U.S. patent application Ser. No. 14/144,280, titled "DEVICES, SYSTEMS, AND METHODS FOR ASSESSMENT OF VESSELS" and filed Dec. 31, 2012, which is hereby incorporated by reference in its entirety. In some embodiments, co-registration and/or correlation can be completed as described in U.S. Provisional Patent Application No. 61/856,509, titled "DEVICES, SYSTEMS, AND METHODS FOR ASSESSMENT OF VESSELS" and filed Jul. 19, 2013, which is hereby incorporated by reference in its entirety. In other embodiments, co-registration and/or correlation can be completed as described in International Application No. PCT/IL2011/000612, titled "CO-USE OF ENDOLUMINAL DATA AND EXTRALUMINAL IMAGING" and filed Jul. 28, 2011, which is hereby incorporated by reference in its entirety. Further, in some embodiments, co-registration and/or correlation can be completed as described in International Application No. PCT/IL2009/001089, titled "IMAGE PROCESSING AND TOOL ACTUATION FOR MEDICAL PROCEDURES" and filed Nov. 18, 2009, which is hereby incorporated by reference in its entirety. Additionally, in other embodiments, co-registration and/or correlation can be completed as described in U.S. patent application Ser. No. 12/075,244, titled "IMAGING FOR USE WITH MOVING ORGANS" and filed Mar. 10, 2008, which is hereby incorporated by reference in its entirety.

Referring now to FIG. 5, shown therein is an exemplary depiction of angiogram data as may be provided to the clinician in a user interface 500, such as may be provided by the computing device 172 of FIG. 4. The user interface 500 includes a window 502 that may be presented in the display 182 as seen in FIG. 4. The window displays angiogram data that includes cardiac tissue 506 and vasculature 508 obtained using a contrast agent. In some embodiments, the angiogram 504 may be a three-dimensional angiogram that may be manipulated by the clinician to provide different views, including different perspective views and/or cross-sectional views, of the patient's vasculature. During subsequent procedures, the clinician may navigate the instruments 130 and/or 132 through the patient's vasculature, collecting physiology measurements therein. The physiology measurements may be stored in a memory of the computing device 172 and also displayed on the display 182. The image-based physiology measurements may include a dominance classification, a degree of occlusion of a lesion, which may be expressed as a percent diameter stenosis, a classification of a lesion, a degree of bending of a vessel of the vessel system, a length of a lesion, and/or a degree of calcification of a lesion. In particular, the status of the system in regards to vessel mapping, lesion identification, and lesion classification may be seen in the windows 510, 520, 530 of the user interface 500. These windows may display the status of the various features with an on/off indicator as shown in FIGS. 5-8. The user interface 500 also allows for selection of a certain area of the image. In this case, no specific area is selected.

After obtaining the angiogram data, the data may be parsed by an image-processing component provided by the system 150 of FIG. 4 to segment the patient's vasculature and estimate certain features thereof. The parsing of the data may be performed to extract image-based physiology measurements which may be automatically displayed without the continued interaction of a clinician. For example, the image-based physiology measurements may be extracted after an angiogram collection process is complete.

When processing the angiogram data, quantitative coronary angiography (QCA) may be used to assess and identify blockages from the image-based data. A QCA process may be initiated automatically to identify any blockages. While the clinician may provide a qualitative evaluation based on his or her own experience, the information from the QCA process may be used in subsequent steps to automatically generate an objective intervention recommendation. As is discussed in further detail below, co-registration techniques incorporated herein by reference and others that may be known to those of skill in the art may be used to co-register physiology measurements to specific positions in a model of the patient's vasculature 508 generated from the angiogram 504 presented in the window 502.

Figure 6:
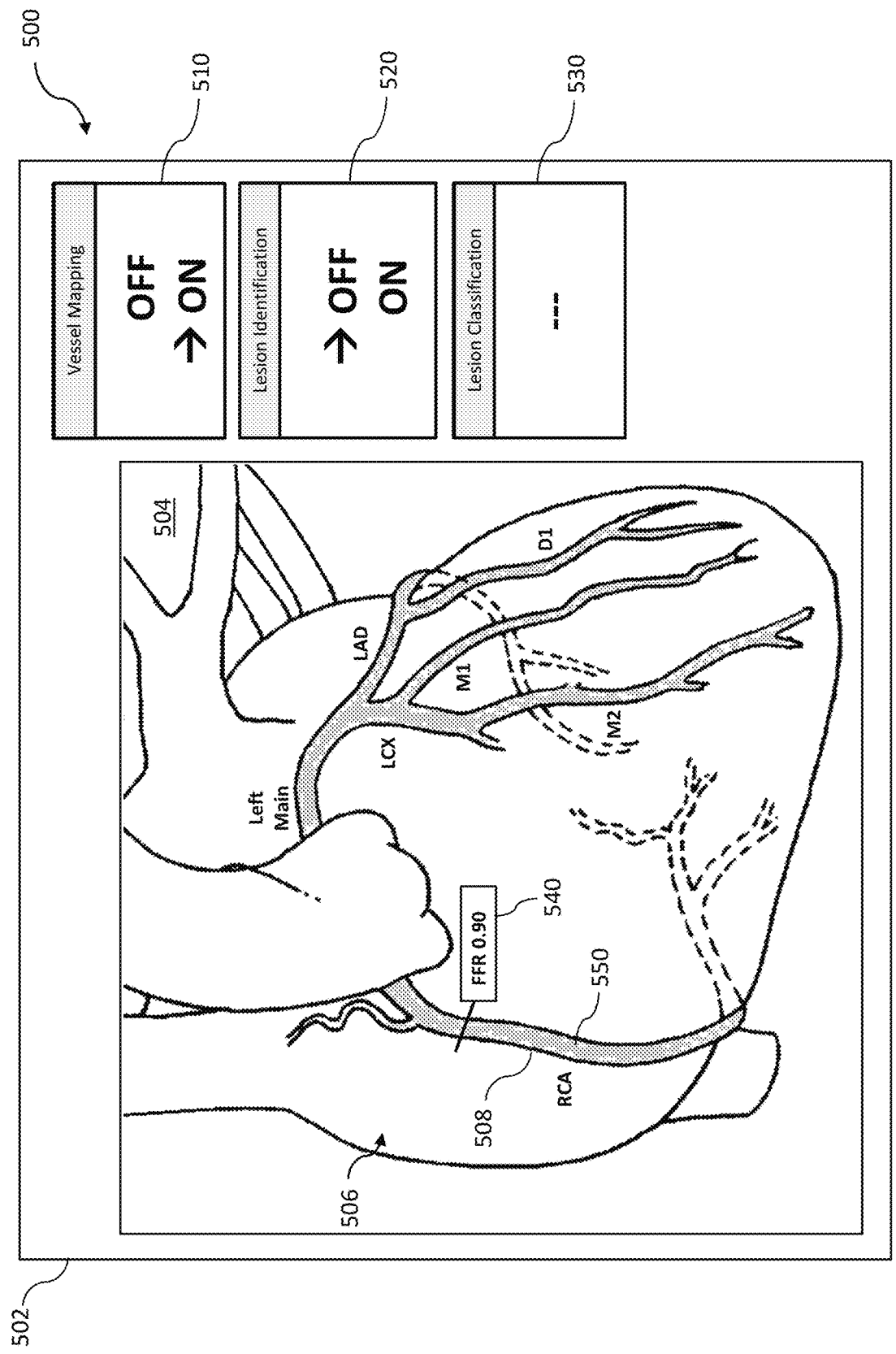
FIG. 6 is an annotated version of a patient's vasculature as seen in an angiogram image on a user interface according to an embodiment of the present disclosure.

Now referring to FIG. 6, the user interface 500 displays data from the various sources as collected and analyzed by the system 150. In particular, the vessel of the patient is actively mapped according to the co-registered data. The status of the system is shown as "on" in the window 510 pertaining to vessel mapping. The user interface 500 may display the mapped vessels as a colored region. The user is able to look at specific regions of the mapped area to observe associated pressure readings and lesion identification and classification. Further, as a result of the vessel mapping the system may label the vessels accordingly. For example, in the illustrated embodiment, the right coronary artery is labeled "RCA," the left main artery is labeled "Left Main," the left circumflex artery is labeled "LCX," the marginal branches are labeled "M1" and "M2," the left anterior descending artery is labeled "LAD," and the diagonal branch is labeled "D1." It is understood that any vessels, including arteries and veins, may be labeled in a similar manner.

Further, a user may select the vessels of interest such that only those vessels are labeled by the system.

Automatic mapping of the vessel system by the system 150 may be accomplished upon performing an image-recognition process on the angiogram information such as that depicted in the user interface 500 of FIG. 5. The angiogram information may include information characterizing or describing features of the vessel system such as the contours, location, branches, and other features of the vessels to automatically identify individual vessels within the patient's vasculature. In this way, a model of the patient's vasculature may be generated and parsed to identify specific sections which a user may observe. Particular vessels which may be identified and mapped by the system 150 include, but are not limited to, right coronary artery (RCA), left main coronary artery (LCA), circumflex coronary artery, left anterior descending (LAD), RCA proximal, RCA mid, RCA distal, LAD proximal, LAD mid, LAD apical, first diagonal, additional first diagonal, second diagonal, additional second diagonal, proximal circumflex, intermediate/anterolateral, obtuse marginal, distal circumflex, left posterolateral, posterior descending, among others.

Markers 540 may be used in conjunction with the mapping of the vessel system. As seen in FIG. 6, an FFR reading is shown at the selected area of the LCA with marker 540. Other physiological readings or anatomical labels may be displayed by markers 540. Markers 540 can also be positioned automatically based on the physiology measurements. The system can be configured to select locations within the vessel that are clinically significant based on the diagnostic information (e.g., locations where the physiology measurements change significantly, such as points at which pressure changes). Similarly, the markers 540 may be provided for various predefined segments of the patient's vasculature. Markers 540 may also be automatically generated based on the angiogram data using image-recognition and modeling techniques. In some embodiments, markers 540 are included automatically by the system 150 upon performing an image-recognition process on the angiogram information. The angiogram information may include, information characterizing or describing features of the vessel system such as the contours, location, branches, and other features of the vessel(s) to automatically identify individual vessels within the patient's vasculature. In this way, a model of the patient's vasculature may be generated and parsed to identify specific sections warranting the appropriate label.

It is understood that numerous other visualization techniques may be utilized to convey the information of FIG. 6 in the context of an angiographic image or other image of the vessel (including both intravascular and extravascular imaging techniques, such as IVUS, OCT, ICE, CTA, etc.) to help the user evaluate the vessel. In that regard, while the examples of the present disclosure are provided with respect to angiographic images, it is understood that the concepts are equally applicable to other types of vessel imaging techniques, including intravascular and extravascular imaging. In some instances, a user is able to select what information should be included or excluded from the displayed image. In that regard, it should be noted that these visualization techniques related to conveying the pressure measurement data in the context of an angiographic or other image of the vessel can be utilized individually and in any combinations. For example, in some implementations a user is able to select what visualization mode(s) and/or portions thereof will be utilized and the system outputs the display accordingly. Further, in some implementations the user is able to manually annotate the displayed image to include notes and/or input one or more of the measured parameters.

The images of vessels in FIG. 6 can include three-dimensional, two-dimensional, angiographic, a computed tomography angiographic (CTA), and/or other suitable forms of images. In some embodiments, a three-dimensional image may be rotated about a vertical axis. In some embodiments, a two-dimensional image may include multiple views about a vertical axis such that different two-dimensional views are shown when the image is rotated. In some implementations, the three dimensional model is displayed adjacent to a corresponding two dimensional depiction of the vessel. In that regard, the user may select both the type of depiction(s) (two dimensional (including imaging modality type) and/or three dimensional) along with what visualization mode(s) and/or portions thereof will be utilized. The system will output a corresponding display based on the user's preferences/selections and/or system defaults.

FIG. 7 shows an exemplary user interface 500 with the vessel mapping and lesion identification features activated. As in FIG. 6, the windows 510, 520 corresponding to the features are labeled as "on." In the embodiment shown, the lesion identification feature displays regions of interest 522, 524 where lesions are likely to be located. The identification of these area may be based on physiology measurements. The system 150 can be configured to select locations within the vessel that are clinically significant based on the diagnostic information (e.g., locations where the physiology measurements change significantly, such as points at which pressure changes). Similarly, the one or more regions of interest may be based on anatomical data the signals heightened risk of lesions, such as the narrowing of a vessel. As seen in FIG. 7, regions of interest 522, 524 can be identified without classifying the lesions that are likely to exist at the defined areas. In this case, window 530 remains blank.

Figure 8:
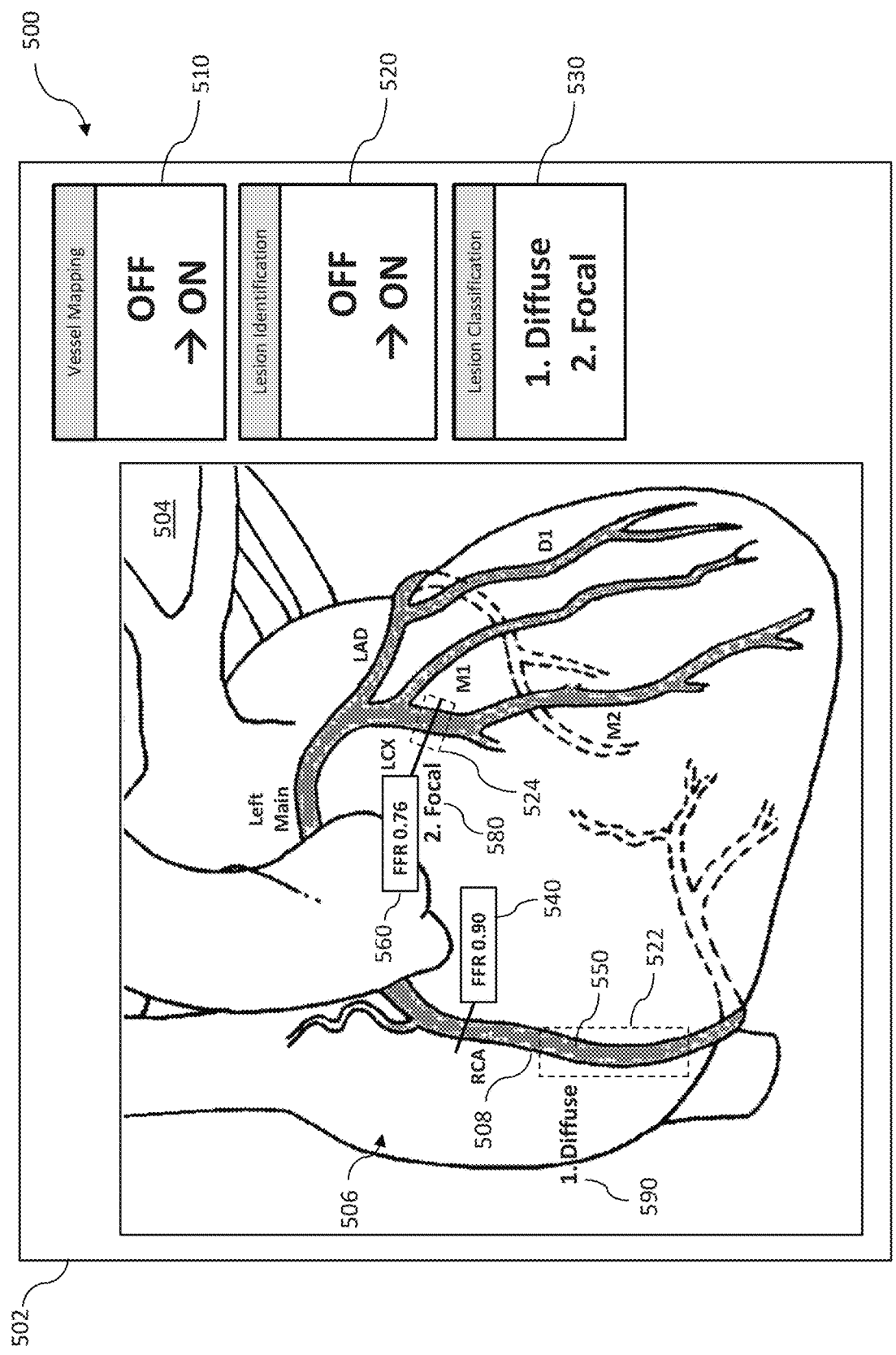
FIG. 8 is an annotated version of a patient's vasculature as seen in an angiogram image on a user interface according to another embodiment of the present disclosure

Referring now to FIG. 8, shown therein is a depiction of a user interface 600 with activated features of vessel mapping, lesion identification, and lesion classification. In this example, the system 150 has identified two regions of interest 522, 524 and has further classified the potential lesions on window 530 and in on the user interface 500 with prompts 580, 590. The classification of the diffuse lesions is based on the steady pressure drop over a long portion of the vessel, while the classification of the focal lesion is based on a sharp pressure drop at certain location on the vessel. Markers 540, 560 may be used in lesion classification. Additionally, markers 540, 560 may be used to further study the identified lesions. For example, maker 560 shows a low pressure reading at the center of the region of interest 524 which may further define the classification as a severe focal lesion. Classifications of lesions will be further discussed in relation to FIG. 9.

Figure 9:
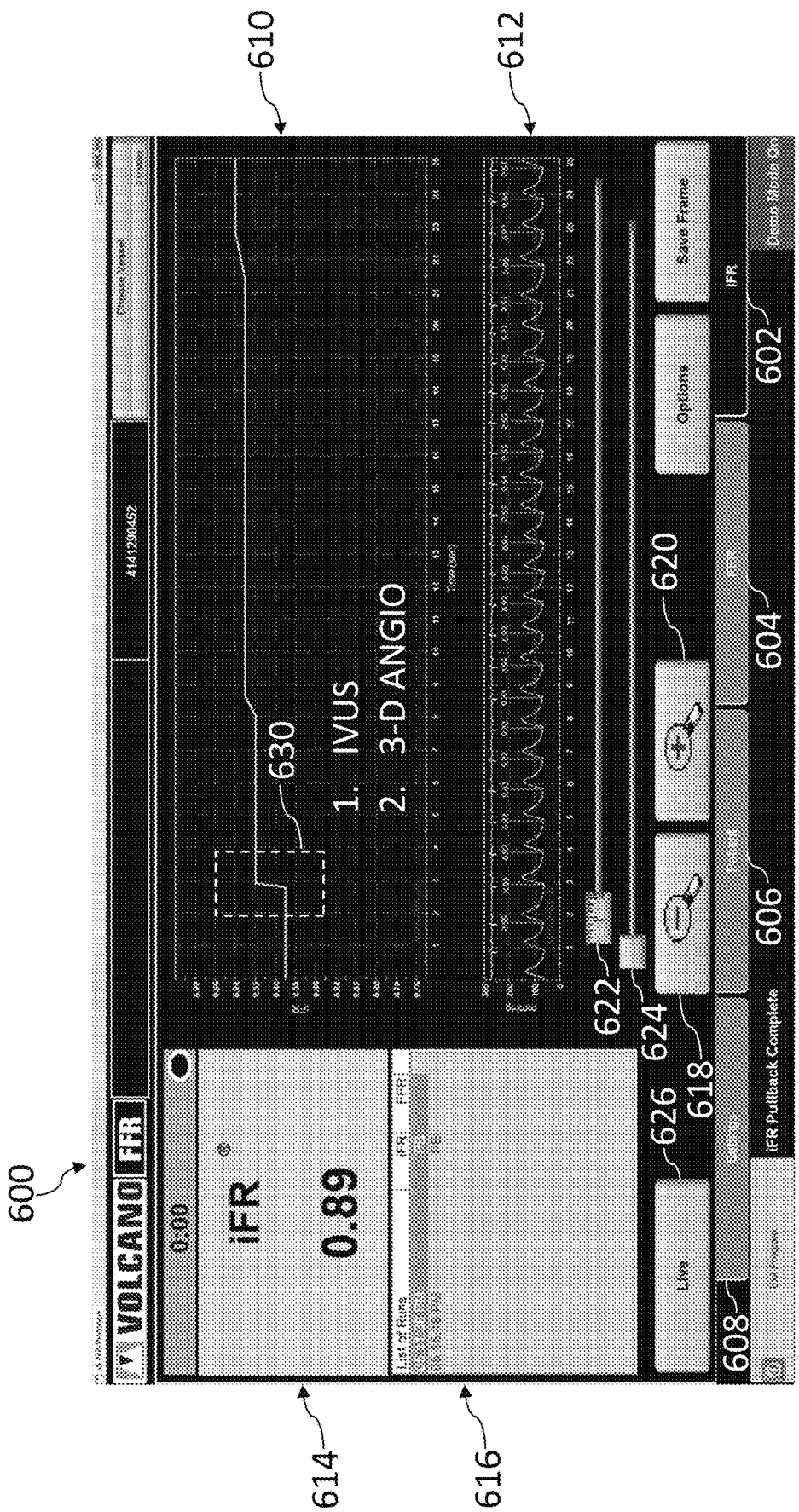
FIG. 9 is a graphical user interface screen display according to an embodiment of the present disclosure.

Referring now to FIG. 9, shown therein is a depiction of a user interface 600 for evaluating a vessel based on obtained physiology measurements (as depicted, pressure measurements, but may also include flow volume, flow velocity, and/or other intravascular physiology measurements or calculations based thereon) according to embodiments of the present disclosure. The user interface may be displayed on a touch-sensitive display. A clinician can view, analyze, and interact with the pressure data and/or visual representations of the pressure data.

Referring more specifically to FIG. 9, shown therein is a screen display 200 according to an embodiment of the present disclosure. The screen display 200 includes multiple tabs, including an iFR tab 202, an FFR tab 204, a patient tab 206, and a settings tab 208. In FIG. 9, the iFR tab 202 has been selected and displayed to a user. As shown, the iFR tab 202 includes a graph 210 and a corresponding pressure waveform plot 212. The screen display 200 also includes a window 214 that shows a calculated pressure ratio (e.g., FFR, iFR, or otherwise). The screen display 200 also includes a window 216 showing the runs or pullbacks available for display to the user. In the illustrated embodiment, two different runs are available and identified by a corresponding time stamp. In that regard, a user can select the desired run from the window 216 and the data shown in the graph 210 and pressure waveform plot 212 will update accordingly.

The screen display 200 also includes zoom buttons 218, 220 that allow a user to zoom out or in, respectively, on the graph 210 and the pressure waveform plot 212. To this end, the screen display 200 includes a ruler 222 showing the relative scale of the graph 210 and the pressure waveform plot 212. In some instances, the ruler 222 provides a dimensional scale of the graphical display of the graph 210 and/or the pressure waveform plot 212 relative to the vessel length and/or the pullback length. The scale of the ruler 222 automatically updates in response to selective actuation of the zoom buttons 218, 220 in some implementations.

The screen display 200 also includes a slider 224. The slider 224 allows the user to move along the length of the vessel and/or the corresponding pullback data. For example, in some instances the left end of the slider 224 corresponds to the beginning of the pullback and the right end of the slider corresponds to the end of the pullback. By moving the slider 224 between the first and second ends, a user can see corresponding portions of the pressure data in the graph 210 and the pressure waveform plot 212. Accordingly, a user can focus on certain portions of the vessel and pullback data using the zoom buttons 218, 220 in combination with the slider 224. In some instances, the numerical value of the pressure ratio displayed in window 214 is updated based on the position of the slider and/or. In that regard, in some instances the numerical value of the pressure ratio displayed in window 214 is based solely on the pressure data being displayed in the graph 210 and the pressure waveform plot 212. However, in other instances the numerical value of the pressure ratio displayed in window 214 is based one of or a combination of the pressure data being displayed in the graph 210 and the pressure waveform plot 212 and pressure data not displayed in the graph 210 and the pressure waveform plot 212.

In that regard, the graph 210 and pressure waveform plot 212 of screen display 200 illustrate aspects of pressure measurements obtained as one instrument is moved through the vessel and another instrument is maintained at a fixed location. In that regard, in some instances the pressure measurements are representative of a pressure ratio between a fixed location within the vessel and the moving position of the instrument as the instrument is moved through the vessel. For example, in some instances a proximal pressure measurement is obtained at a fixed location within the vessel while the instrument is pulled back through the vessel from a first position distal of the position where the proximal pressure measurement is obtained to a second position more proximal than the first position (i.e., closer to the fixed position of the proximal pressure measurement). For clarity in understanding the concepts of the present disclosure, this arrangement will be utilized to describe many of the embodiments of the present disclosure. However, it is understood that the concepts are equally applicable to other arrangements. For example, in some instances, the instrument is pushed through the vessel from a first position distal of the proximal pressure measurement location to a second position further distal (i.e., further away from the fixed position of the proximal pressure measurement). In other instances, a distal pressure measurement is obtained at a fixed location within the vessel and the instrument is pulled back through the vessel from a first position proximal of the fixed location of the distal pressure measurement to a second position more proximal than the first position (i.e., further away from the fixed position of the distal pressure measurement). In still other instances, a distal pressure measurement is obtained at a fixed location within the vessel and the instrument is pushed through the vessel from a first position proximal of the fixed location of the distal pressure measurement to a second position less proximal than the first position (i.e., closer the fixed position of the distal pressure measurement).

The pressure differential between the two pressure measurements within the vessel (e.g., a fixed location pressure measurement and a moving pressure measurement) is calculated as a ratio of the two pressure measurements (e.g., the moving pressure measurement divided by the fixed location pressure measurement), in some instances. In some instances, the pressure differential is calculated for each heartbeat cycle of the patient. In that regard, the calculated pressure differential is the average pressure differential across a heartbeat cycle in some embodiments. For example, in some instances where a hyperemic agent is applied to the patient, the average pressure differential across the heartbeat cycle is utilized to calculate the pressure differential. In other embodiments, only a portion of the heartbeat cycle is utilized to calculate the pressure differential. The pressure differential is an average over the portion or diagnostic window of the heartbeat cycle, in some instances.

In some embodiments a diagnostic window is selected using one or more of the techniques described in U.S. patent application Ser. No. 13/460,296, filed Apr. 30, 2012 and titled "DEVICES, SYSTEMS, AND METHODS FOR ASSESSING A VESSEL," which is hereby incorporated by reference in its entirety. As discussed therein, the diagnostic windows and associated techniques are particularly suitable for use without application of a hyperemic agent to the patient. In general, the diagnostic window for evaluating differential pressure across a stenosis without the use of a hyperemic agent is identified based on characteristics and/or components of one or more of proximal pressure measurements, distal pressure measurements, proximal velocity measurements, distal velocity measurements, ECG waveforms, and/or other identifiable and/or measurable aspects of vessel performance. In that regard, various signal processing and/or computational techniques can be applied to the characteristics and/or components of one or more of proximal pressure measurements, distal pressure measurements, proximal velocity measurements, distal velocity measurements, ECG waveforms, and/or other identifiable and/or measurable aspects of vessel performance to identify a suitable diagnostic window.

In the illustrated embodiment of FIG. 9, the graph 210 shows the pressure ratio over time. In particular, the graph 210 shows the pressure ratio calculated over the time of a pullback. More specifically, the graph 210 shows an iFR pressure ratio value during a pullback. In that regard, the iFR pressure ratio may be calculated as described in one or more of PCT Patent Application Publication No. WO 2012/093260, filed Jan. 6, 2012 and titled "APPARATUS AND METHOD OF CHARACTERISING A NARROWING IN A FLUID FILLED TUBE," PCT Patent Application Publication No. WO 2012/093266, filed Jan. 6, 2012 and titled "APPARATUS AND METHOD OF ASSESSING A NARROWING IN A FLUID FILLED TUBE," U.S. patent application Ser. No. 13/460,296, filed Apr. 30, 2012 and titled "DEVICES, SYSTEMS, AND METHODS FOR ASSESSING A VESSEL," PCT Patent Application Publication No. WO 2013/028612, filed Aug. 20, 2012 and titled "DEVICES, SYSTEMS, AND METHODS FOR VISUALLY DEPICTING A VESSEL AND EVALUATING TREATMENT OPTIONS," U.S. Provisional Patent Application No. 61/856,509, filed Jul. 19, 2013 and titled "DEVICES, SYSTEMS, AND METHODS FOR ASSESSMENT OF VESSELS," and U.S. Provisional Patent Application No. 61/856,518, filed Jul. 19, 2013 and titled "DEVICES, SYSTEMS, AND METHODS FOR ASSESSING A VESSEL WITH AUTOMATED DRIFT CORRECTION," each of which is hereby incorporated by reference in its entirety.

The graph 210 can illustrate the pressure ratio and/or the underlying pressure measurements in any suitable way. Generally speaking, the representation of the data in graph 210 can be utilized to identify gradients/changes in the pressure ratio and/or the underlying pressure measurements that can be indicative of a significant lesion in the vessel. In that regard, the visual representation of the data can include the pressure measurement(s); a ratio of the pressure measurements; a difference in the pressure measurements; a gradient of the pressure measurement(s), the ratio of the pressure measurements, and/or the difference in the pressure measurements; first or second derivatives of the pressure measurement(s), the ratio of the pressure measurements, and/or the difference in the pressure measurements; and/or combinations thereof.

Likewise, the pressure waveform plot 212 shows the corresponding pressure data. In that regard, the pressure waveform plot 212 can include the pressure waveform for the pressure sensing device moved through the vessel during the pullback, the pressure waveform for the stationary pressure sensing device, or both. In the illustrated embodiment, the pressure waveform plot 212 includes the pressure waveforms for both. In some instances the pressure waveform plot 212 is augmented to highlight or otherwise accentuate the pressure data corresponding to the diagnostic window utilized for the pressure ratio calculations.

As shown in FIG. 9, the screen display 200 includes a button 226 indicating that the data is being displayed in a "Live" mode, which indicates that the screen display 200, including graph 210, pressure waveform plot 212, and/or the window 214, is being updated in real time as a procedure is being performed. In other instances, the button 226 of the screen display 200 will indicated that it is in "Playback" or "Review" mode, which indicates that the screen display 200 is showing data obtained previously. With respect to the "Live" mode, it should be noted that the determination of the diagnostic window and/or the calculation of the pressure differential are performed in approximately real time or live to identify the diagnostic window of the heartbeat cycle and calculate the pressure differential. In that regard, calculating the pressure differential in "real time" or "live" within the context of the present disclosure is understood to encompass calculations that occur within 10 seconds of data acquisition. It is recognized, however, that often "real time" or "live" calculations are performed within 1 second of data acquisition. In some instances, the "real time" or "live" calculations are performed concurrent with data acquisition. In some instances the calculations are performed by a processor in the delays between data acquisitions. For example, if data is acquired from the pressure sensing devices for 1 ms every 5 ms, then in the 4 ms between data acquisitions the processor can perform the calculations. It is understood that these timings are for example only and that data acquisition rates, processing times, and/or other parameters surrounding the calculations will vary. In other embodiments, the pressure differential calculation is performed 10 or more seconds after data acquisition. For example, in some embodiments, the data utilized to identify the diagnostic window and/or calculate the pressure differential are stored for later analysis.

By comparing the calculated pressure differential to a threshold or predetermined value, a physician or other treating medical personnel can determine what, if any, treatment should be administered. In that regard, in some instances, a calculated pressure differential above a threshold value (e.g., 0.80 on a scale of 0.00 to 1.00) is indicative of a first treatment mode (e.g., no treatment, drug therapy, etc.), while a calculated pressure differential below the threshold value is indicative of a second, more invasive treatment mode (e.g., angioplasty, stent, etc.). In some instances, the threshold value is a fixed, preset value. In other instances, the threshold value is selected for a particular patient and/or a particular stenosis of a patient. In that regard, the threshold value for a particular patient may be based on one or more of empirical data, patient characteristics, patient history, physician preference, available treatment options, and/or other parameters.

Also shown on FIG. 9 is region of interest 630. The region of interest 630 may be assigned by the system 150 based on anomalous readings from the instruments such as drastic pressure changes in the vessel. In this embodiment, the region of interest 630 is centered around a sharp pressure change in the vessel. When such an region of interest 630 is identified by the system 150, the screen display 200 may show one or more options for taking further diagnostic measurements of the region of interest 630. Therefore, the screen display 200 as shown in FIG. 9 prompts a medical professional to perform an IVUS measurement on the identified section of the vessel which may be further confirmed by a three-dimensional angiogram.

The coloring and/or other visually distinguishing aspect of the pressure differential measurements depicted in graph 210 and/or window 214 of the screen display 200 of FIG. 9 are configured based on the threshold value in some instances. For example, a first color (e.g., green, white, or otherwise) can be utilized to represent values well above the threshold value (e.g., where the threshold value is 0.80 on a scale of 0.00 to 1.00, values above 0.90), a second color (e.g., yellow, gray, or otherwise) can be utilized to represent values near but above the threshold value (e.g., where the threshold value is 0.80 on a scale of 0.00 to 1.00, values between 0.81 and 0.90), and a third color (e.g., red, black, or otherwise) can be utilized to represent values equal to or below the threshold value (e.g., where the threshold value is 0.80 on a scale of 0.00 to 1.00, values of 0.80 and below). Further, in some instances the graph 210 includes one or more horizontal lines or other depictions representing the threshold value(s). It is appreciated that any number of color combinations, scalings, categories, and/or other characteristics can be utilized to visually represent the relative value of the pressure differential to the threshold value. However, for the sake of brevity Applicants will not explicitly describe the numerous variations herein.

Figure 10:
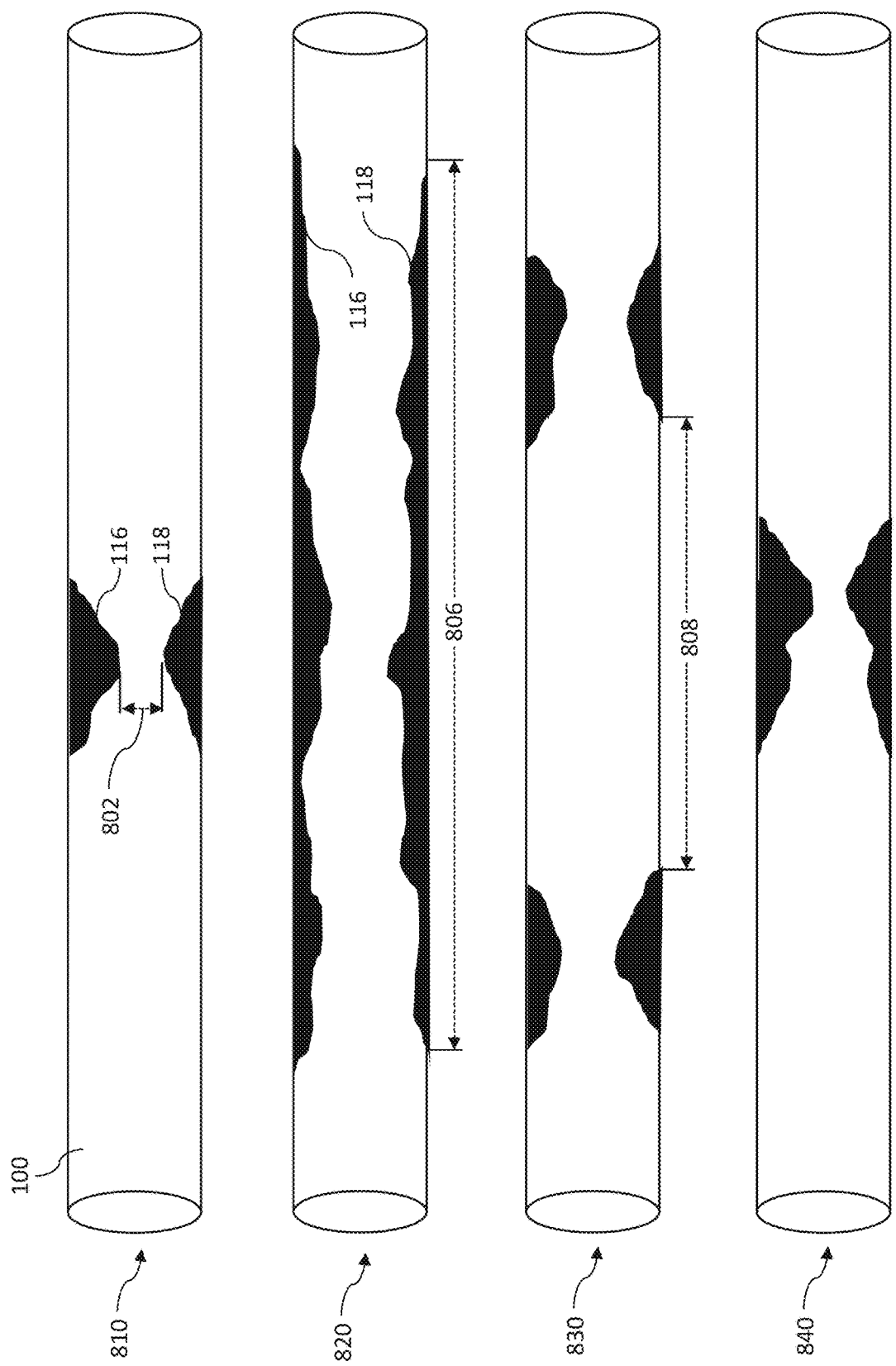
FIG. 10 is a series of stylized images of a vessel illustrating classification of vessel obstructions according to an embodiment of the present disclosure.

FIG. 10 shows diagrams of several classifications of lesions that may be identified by the system 150, including "focal," "moderate," "severe," "diffuse," "long," "short," "multiple," and "multi." Lesion 810 is made up of plaque buildup on both an upper portion 116 and lower portion 118 of a vessel 100. A decrease in the distance 802 between the upper and lower portions 116, 118 of the plaque buildup leads to a decrease in pressure because the plaque buildup decreases the available space for fluid to flow through the vessel 100. This pressure drop may also be referred to a as the functional intensity of the lesion. The classification of the lesion can be derived from the functional intensity and the length of the pressure drop across the vessel 100. In particular, the functional intensity or slope of the pressure loss may be mapped to a length of the vessel using techniques such as co-registration of physiologic measurements such as FFR, iFR, CFR, and angiography, and the results of the analysis may be compared to a classification index containing the lesions classifications as described below.

Lesion 810 causes a sharp pressure loss over a relatively short length and is classified as "focal." Focal lesions may vary greatly in severity, and may be further classified according to how much they decrease the cross section if the vessel 100. This may be measured by either a distance 802 or a percentage of the vessel that is constricted. Because lesions may occur in vessels of many different sizes, classification by a percentage may be favored. In some cases, "moderate" focal lesions narrow the vessel 100 by 20-60%, whereas "severe" focal lesions narrow the vessel 100 by 60-100%.

In contrast to the focal lesion focal lesions, other lesions cause a gradual pressure drop over a longer length of the vessel. For example, lesion 820 is classified as "diffuse." As shown, diffuse lesions often exhibit uneven plaque buildup along the length of the vessel 100. Diffuse lesions may be further classified based on their length 806 (i.e., the distance along the vessel 100 that the plaque extends on both sides of the vessel). In one embodiment, lesions with a length of over 5 mm are classified as "long," while lesions measuring 5 mm or less are classified as "short." In some instances, multiple lesions exist within a vessel 100, such as those shown in example 830. Where the lesions are close together, example 830 may be considered as a "multiple" lesion classification. The distance 808 between lesions may determine if they are separate focal lesions or a combined multiple lesion. In one embodiment, where the lesions are less than 10 mm apart, they may be considered as a multiple lesion. Lesion 840 shows complex plaque buildup forms on both sides of the vessel 100. In this case, two lesions overlap within the vessel and the lesion 840 may be classified as "multi." This classification includes multiple lesions located close together so that there is no distance 808 between their areas of plaque buildup, while narrowed sections occur at two or more points along the vessel 100. The classification process of the present disclosure may involve examining the vessel anatomy at the point of the suspected lesion. In particular, the presence of plaque around a vessel bifurcation can lead to anomalous classifications because pressure reading may vary widely as a result of the bifurcation.

Figure 11:
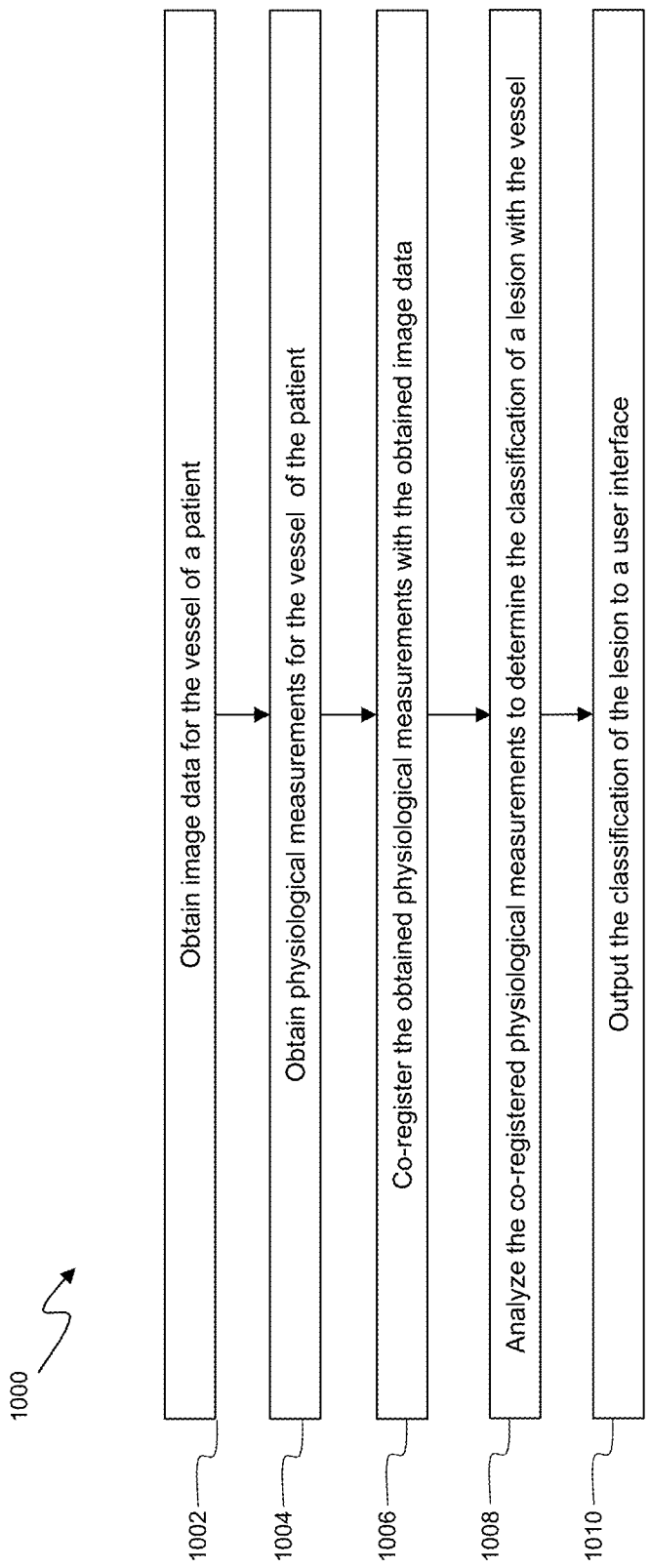
FIG. 11 is a flow diagram of a method for identify and classifying lesions with an vessel system according to an embodiment of the present disclosure.

FIG. 11 is a flow diagram of a method 1000 of evaluating a vessel system of a patient to identify and classify a lesion in the vessel of a patient according to an embodiment of the present disclosure. Method 1000 can be implemented by a system described herein, such as system 150 of FIG. 4. As illustrated in FIG. 11, the method 1000 is illustrated as a plurality of enumerated steps or operations. Embodiments of the method 1000 may include additional steps or operations before, after, in between, or as part of the enumerated steps. At step 1002, method 1000 can include obtaining image data from an image of a vessel system. This may be done by contacting networked storage such as an electronic health record storage system to obtain image data, such as angiogram data. The angiogram data may include a two dimensional angiographic image, a three dimensional angiographic image, and/or a computed tomography angiographic (CTA) image. An example of the angiogram data may be seen in the user interface 500 of FIGS. 5-8, which includes the angiogram 504.

At step 1004, the method 1000 can include obtaining physiology measurements from a first instrument and a second instrument positioned within the vessel of the patient while the second instrument is moved longitudinally through the vessel from a first position to a second position. One or more diagnostic measurements (e.g., pressure-based including FFR and iFR, flow-based including CFR, etc.) can be used to gather the physiology measurements to characterize the existence and/or severity of a lesion or lesions within the vasculature of a patient. For example, when FFR is used, areas of a patient's vasculature that have a relatively high FFR (e.g., greater than 0.80) are characterized as not having a lesion or stenosis, while areas with a relatively low FFR (e.g., less than 0.80) are characterized as having a lesion or stenosis. The physiology measurements may be obtained in a manner that provides at least some location information associated with the measurements.

At step 1006, the method 1000 can include co-registering the physiology measurements with the image data to produce co-registered physiology measurements. The co-registered physiology measurements can be displayed in an overlaid fashion, such that the physiology measurements may be visualized in association with the angiogram image data. An example may be seen in the user interface 500 of FIGS. 5-8. By co-registering the physiology measurements with the image data, the system 150 may provide additional perspective to a clinician or clinicians. The imagery may indicate the physical dimensions of the patient's vasculature, which may be sufficient to identify one or more lesions therein, while the physiology measurements indicate the impact or effect of lesions with the vasculature. In some embodiments, co-registering the physiology measurements with the image data may include associating, in a data file, each physiology measurement with a location within the vessel system, identifying a corresponding location for each physiology measurement with the image data, and associating in the co-registered physiology measurements data file, each physiology measurement with its corresponding location within the image of the vessel system. In some embodiments, co-registering the physiology measurements may produce a new data file that includes the co-registered physiology measurements.

Co-registration may also be accomplished by overlaying the data from imaging systems (such as angiographic images, x-ray images, CT images, PET images, MRI images, SPECT images, and/or other two-dimensional or three-dimensional extraluminal depictions of a patient's vasculature) with data obtained by instruments 130, 132, 152, and/or 175 of the system 150 (as shown in FIG. 4). In some cases, information characterizing or describing features of the vessel system such as the contours, location, branches, and other features of the vessels are used to automatically identify individual vessels within the patient's vasculature and serve as a baseline for compiling a complete vessel map for a patient.

At step 1008, the method 1000 can include analyzing the co-registered physiological measurements to determine the classification of a lesion within the vessel. Potential regions of interest where a lesion may be located are identified by the system 150 based on co-registered pressure readings and anatomical context of the readings. Potential lesion locations may also be based on anatomical physiological data such as unexpected narrowing of a vessel or the existence of a side branch near a stenosis. Further physiology information that may be considered in the identification includes dominance classification, a degree of occlusion of the lesion area, a degree of bending of a vessel of the vessel system, a degree of calcification of the lesion area, etc. The identification may also be based on a comparison of current physiological measurements with previously recorded physiological measurements from a database. Other sources of information that form part of the analysis and formulation of the recommendation include patient history such as age, gender, or preexisting conditions such as diabetes or hypertension. After identifying potential lesions, the system 150 classifies the lesions based on functional parameters. Generally, the classification relies on the cardiovascular pressure intensity and lesion length measurements. Classifications of lesions that may be identified by the system 150 include "focal," "moderate," "severe," "diffuse," "long," "short," "multiple," "multi," or other suitable classification. The criteria for making each of these classifications is discussed in conjunction with FIG. 10.

At step 1010, the method 1000 can include displaying the identification and classification of the lesion to a user. In some embodiments, this information is automatically displayed on a user interface 500 such as that shown in FIGS. 5-8. The identification and classification may be read by medical professionals during the course of a procedure to help guide diagnoses. Additionally, the identification and classification may be used as an educational too. For instance, the identification of the lesion and factors used by the system 150 in the analysis used to formulate the identification may be presented to a patient, or the family members or guardian of a patient to help explain the reasoning of the medical professional or the likelihood of future procedures.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of evaluating a vessel of a patient, the method comprising:
    communicating, via a processing system, with an x-ray imaging device to obtain an x-ray image of the vessel of the patient;
    controlling, by the processing system, a guidewire or a catheter positioned within the vessel of the patient to acquire pressure measurements of the vessel of the patient via a pressure sensor of the guidewire or catheter, wherein the pressure sensor is coupled to a distal portion of the guidewire or catheter;
    determining, by the processing system, a plurality of pressure ratios based on the pressure measurements and associated with a plurality of locations within the vessel;
    co-registering, by the processing system, the plurality of pressure ratios with the x-ray image such that each pressure ratio of the plurality of pressure ratios is associated with a corresponding location of the vessel of the patient;
    identifying, by the processing system, a location of a lesion within the vessel based on a change in the plurality of co-registered pressure ratios between the plurality of locations;
    determining, by the processing system, a value of the change in the plurality of co-registered pressure ratios;
    determining, by the processing system, a classification of the lesion based on the location of the lesion and the value of the change in the plurality of co-registered pressure ratios, wherein the classification corresponds to a spatial description of plaque buildup within the vessel, and wherein determining the classification of the lesion comprises determining if the lesion is focal or diffuse; and
    outputting, by the processing system, a graphical representation of the classification of the lesion at the location of the lesion in the x-ray image to a user interface.

2. The method of claim 1, further comprising:
    analyzing the x-ray image to identify an anatomical name for the vessel; and
    outputting, to the user interface, a label indicating the anatomical name for the vessel in proximity to the vessel.

3. The method of claim 2, wherein analyzing the x-ray image to identify the anatomical name for the vessel includes utilizing a computer aided detection algorithm.

4. The method of claim 1, wherein the x-ray image includes at least one of a two-dimensional angiographic image, a three-dimensional angiographic image, or a computed tomography angiographic (CTA) image.

5. The method of claim 1, wherein at least some of the pressure measurements are acquired at multiple locations along the vessel.

6. A system for evaluating a vessel of a patient, the system comprising:
    a guidewire or catheter configured to be positioned within the vessel of the patient, wherein the guidewire or catheter comprises a pressure sensor configured to acquire pressure measurements of the vessel of the patient, wherein the pressure sensor is coupled to a distal portion of the guidewire or catheter; and
    a processing system in communication with the guidewire or catheter, the processing system configured to:
        communicate with an x-ray imaging device to obtain an x-ray image of the vessel of the patient;
        control the guidewire or catheter to acquire the pressure measurements via the pressure sensor;
        determine, based on the pressure measurements, a plurality of pressure ratios associated with a plurality of locations within the vessel;
        co-register, by the processing system, the plurality of pressure ratios with the x-ray image such that each pressure ratio of the plurality of pressure ratios is associated with a corresponding location of the vessel of the patient;
        identify a location of a lesion within the vessel based on a change in the plurality of co-registered pressure ratios between the plurality of locations;
        determine, a value of the change in the plurality of co-registered pressure ratios;

determine a classification of the lesion based on the location of the lesion and the value of the change in the plurality of co-registered pressure ratios, wherein the classification corresponds to a spatial description of plaque buildup within the vessel, and wherein the processing system is configured to determine the classification of the lesion by determining if the lesion is focal or diffuse; and output a graphical representation of the classification of the lesion at the location of the lesion in the x-ray image to a user interface.

7. The system of claim 6, wherein the processing system is further configured to:

analyze the x-ray image to identify an anatomical name for the vessel; and output, to the user interface, a label indicating the anatomical name for the vessel in proximity to the vessel.

8. The system of claim 7, wherein the processing system utilizes a computer aided detection algorithm to identify the anatomical name for the vessel.

9. The system of claim 6, wherein the x-ray image includes at least one of a two-dimensional angiographic image, a three-dimensional angiographic image, or a computed tomography angiographic (CTA) image.

10. The method of claim 1, wherein determining the classification of the lesion comprises determining the classification of the lesion based on the value of the change in the plurality of co-registered pressure ratios relative to a value of a length of the vessel.

11. The method of claim 1, further comprising calculating, based on the plurality of co-registered pressure ratios, a slope of a pressure loss, wherein the classification is determined based on the slope of the pressure loss.

12. The system of claim 6, wherein the processing system is further configured to:

determine, based on the x-ray image, a value associated with the spatial description of plaque within the vessel, wherein the processing system is configured to determine the classification of the lesion based on the value associated with the spatial description of plaque within the vessel and the value of the change in the plurality of pressure ratios.

13. The system of claim 12, wherein the value associated with the spatial description of plaque within the vessel comprises at least one of:

a percentage of occlusion of the vessel caused by the lesion;

a first distance between a first portion and a second portion the lesion, wherein the first distance is in a direction transverse to a longitudinal axis of the vessel;

a length of the lesion; or a second distance between the lesion and a different lesion longitudinally spaced from the lesion.

14. The system of claim 6, wherein the pressure sensor comprises at least one of a transducer, a piezo-resistive pressure sensor, a piezo-electric pressure sensor, a capacitive pressure sensor, an electromagnetic pressure sensor, a fluid column, or an optical pressure sensor.

* * * * *